United States Patent
Franzusoff et al.

(10) Patent No.: US 8,153,136 B2
(45) Date of Patent: Apr. 10, 2012

(54) YEAST-BASED VACCINES AS IMMUNOTHERAPY

(75) Inventors: Alex Franzusoff, Denver, CO (US); Donald Bellgrau, Highlands Ranch, CO (US)

(73) Assignees: GlobeImmune, Inc., Louisville, CO (US); The Regents of the University of Colorado, Denver, CO (US)

( * ) Notice: Subject to any disclaimer, the term of this patent is extended or adjusted under 35 U.S.C. 154(b) by 144 days.

(21) Appl. No.: 12/334,729

(22) Filed: Dec. 15, 2008

(65) Prior Publication Data
US 2009/0142366 A1    Jun. 4, 2009

Related U.S. Application Data

(63) Continuation of application No. 10/738,646, filed on Dec. 16, 2003, now Pat. No. 7,465,454.

(60) Provisional application No. 60/434,163, filed on Dec. 16, 2002.

(51) Int. Cl.
*A61K 39/00* (2006.01)

(52) U.S. Cl. .................................................. 424/184.1

(58) Field of Classification Search ........................ None
See application file for complete search history.

(56) References Cited

U.S. PATENT DOCUMENTS

| | | | |
|---|---|---|---|
| 4,320,194 A | 3/1982 | Bull | |
| 4,725,550 A | 2/1988 | Perucho et al. | |
| 4,775,622 A | 10/1988 | Hitzeman et al. | |
| 4,871,838 A | 10/1989 | Bos et al. | |
| 5,310,654 A | 5/1994 | Isberg et al. | |
| 5,413,914 A | 5/1995 | Franzusoff | |
| 5,527,676 A | 6/1996 | Vogelstein et al. | |
| 5,744,144 A | 4/1998 | Finn et al. | |
| 5,830,463 A * | 11/1998 | Duke et al. | 424/93.51 |
| 5,833,975 A | 11/1998 | Paoletti et al. | |
| 5,847,095 A | 12/1998 | Bos et al. | |
| 5,858,378 A | 1/1999 | Bostwick | |
| 5,919,651 A | 7/1999 | Hitzeman et al. | |
| 5,942,235 A | 8/1999 | Paoletti | |
| 5,961,978 A | 10/1999 | Gaudernack et al. | |
| 6,090,546 A | 7/2000 | Breivik et al. | |
| 6,107,457 A | 8/2000 | Arlinghaus et al. | |
| 6,187,307 B1 | 2/2001 | Cohen | |
| 6,482,407 B2 | 11/2002 | Soo Hoo | |
| 6,558,951 B1 | 5/2003 | Tomai et al. | |
| 6,759,046 B1 | 7/2004 | Gaudernack et al. | |
| 6,861,057 B2 | 3/2005 | Gaudernack et al. | |
| 6,923,958 B2 | 8/2005 | Xiang et al. | |
| 7,083,787 B2 | 8/2006 | Duke et al. | |
| 7,439,042 B2 | 10/2008 | Duke et al. | |
| 7,465,454 B2 | 12/2008 | Franzusoff et al. | |
| 2002/0044948 A1 | 4/2002 | Khleif et al. | |
| 2002/0155108 A1 | 10/2002 | Barbera-Guillem | |
| 2003/0035810 A1 | 2/2003 | Caplan | |
| 2004/0072759 A1 | 4/2004 | Gaudernack et al. | |
| 2004/0171796 A1 | 9/2004 | Schlom et al. | |
| 2005/0074849 A1 | 4/2005 | Gaudernack et al. | |
| 2007/0048860 A1 | 3/2007 | Schlom et al. | |
| 2007/0166323 A1 | 7/2007 | Duke et al. | |
| 2007/0172503 A1 | 7/2007 | Selitrennikoff et al. | |
| 2007/0224208 A1 | 9/2007 | Guo et al. | |
| 2008/0003239 A1 | 1/2008 | Duke et al. | |
| 2008/0069831 A1 | 3/2008 | Duke et al. | |
| 2008/0069833 A1 | 3/2008 | Franzusoff et al. | |
| 2008/0107671 A1 | 5/2008 | Duke et al. | |
| 2009/0074805 A1 | 3/2009 | Duke et al. | |
| 2009/0304741 A1 | 12/2009 | Duke et al. | |
| 2010/0034840 A1 | 2/2010 | Apelian et al. | |
| 2010/0104604 A1 | 4/2010 | Selitrennikoff et al. | |
| 2010/0111912 A1 | 5/2010 | Apelian et al. | |

FOREIGN PATENT DOCUMENTS

| | | |
|---|---|---|
| EP | 0414404 | 2/1991 |
| FR | 2486400 | 1/1982 |
| JP | 04-506298 | 11/1992 |
| JP | 10-510246 | 10/1998 |
| WO | WO 91/00356 | 1/1991 |
| WO | WO 92/14756 | 9/1992 |
| WO | WO 94/04171 | 3/1994 |
| WO | WO 97/40156 | 10/1997 |
| WO | WO 99/19478 | * 4/1999 |
| WO | WO 00/34494 | 6/2000 |
| WO | WO 00/66153 | 11/2000 |
| WO | WO 01/29233 | 4/2001 |
| WO | WO 01/82963 | 11/2001 |
| WO | WO 02/39951 | 5/2002 |

OTHER PUBLICATIONS

Marshall et al (J Clin Oncol, 1999, 17(1): 332-337).*
Kantor et al (Cancer Research, 1992, 52: 6917-6925).*
McLaughlin et al (Cancer Research, 1996, 56: 2361-2367).*
Abrams et al (J Immunother 1997, 20(1): Abstract).*
Stubbs et al (Nature Medicine, 2001, 7(5): 625-629).*
Wansley et al (Clin Cancer Res, 2008, 14(13): 4316-4325).*
U.S. Appl. No. 12/334,774, filed Dec. 15, 2008, Franzusoff et al. U.S. Appl. No. 12/335,094, filed Dec. 15, 2008, Franzusoff et al.
Ben-Efraim, S. (Tumor Biology 1999; 20: 1-24).
Bodey et al. (Anticancer Research 2000; 20: 2665-2676).
Byers, T. (CA Journal, vol. 49, No. 6, Nov./Dec. 1999).
Frazer, I. (Expert. Opin. Pharmacother. 2004; 5: 2427-2434).
Granziero et al. (Eur. J. Immunol. 1999, 29: 1127-1138).
Marincola et al. (Trends in Immunology 2003;24:334-341).
North (Adv. Immunol 1984; 35: 89-155).
Rosenberg et al. (The New England Journal of Cancer 2004; 350: 1461-1463).
Schlegel et al. (Journal of Neuro-Oncology 1992; 14: 93-100).
Adams et al. International Reviews of Immunology, vol. 11 No. 2, pp. 133-141 (1994).

(Continued)

*Primary Examiner* — Sean Aeder
(74) *Attorney, Agent, or Firm* — Sheridan Ross P.C.

(57) ABSTRACT

Compositions and methods for treating and/or preventing a variety of diseases and conditions that are amenable to immunotherapy and, in one particular embodiment, compositions and methods for treating and/or preventing cancer in an animal are described. Specifically improvements related to the use of a yeast-based vaccine comprising a yeast vehicle and an antigen that is selected to elicit an antigen-specific cellular and humoral immune response in an animal, for use in prophylactic and/or therapeutic vaccination and the prevention and/or treatment of a variety of diseases and conditions are disclosed.

23 Claims, 7 Drawing Sheets

OTHER PUBLICATIONS

Allsopp et al., European Journal of Immunology, vol. 26 No. 8, pp. 1951-1959 (1996).
Bachmann et al., 1994, Curr. Op. Immunol., 6:320-326.
Baker et al., 1988, Cell, 54:335-344.
Bizzini et al., 1990, FEMS Microbiol. Immunol., 64:155-168.
Bourdette et al., 1994, J. Immunol., 152:2510-2519.
Brake et al., 1984, Proc. Natl. Acad. Sci. USA, 81:4642-4646.
Brossier et al., Infection and Immunity, vol. 67, No. 2, Feb. 1999, pp. 964-967.
Brown, D., 1995, The Washington Post, "Gene Therapy 'Oversold' by Researchers, Journalists".
Chou et al., 1994, J. Immunol., 152:2520-2529.
Coghlan, 1995, New Scientists, 145:14-15.
Cohen, 1994, Science, 264:1660.
Cohen, 1994, Science, 264:1839.
Davies et al., 1992, Nucleic Acids Res., 20(11):2693-2698.
Demmer et al., 1993, J. Immunol., 150(12):5371-5378.
Engelhardt et al., 1994, Hum. Gene Ther, 5:1217-1229.
Fattal-German et al., 1992, Develop. Biol. Standard., 77:115-120.
Franzusoff et al., 1995, J. Biol. Chem., 270(7):3154-3159.
Fujita et al., 1987, Bulletin of the World Health Organization, 65(3):303-308.
Garber et al., AIDS Reviews, vol. 5 No. 3, pp. 131-139 (2003).
Gnirke et al., 1991, EMBO J., 10(7):1629-1634.
Gobin et al., 1995, Gene, 163:27-33.
Hatsuyama et al., 1994, Plant Cell Physiol., 35(1):93-98.
Kaur et al., Topics in HIV Medicine, vol. 11 No. 3, pp. 76-85 (2003).
Ketner et al., 1994, Proc. Natl. Acad. Sci. USA, 91:6186-6190.
Layton et al. Immunology, vol. 87 No. 2, pp. 171-178 (1996).
Markie et al., 1993, Somat. Cell Mol. Genet., 19(2):161-169.
Marshall, 1995, Science 269:1050-1055.
Moore et al., 1996, FASEB J., 10(6) Abstract 2725.
Moulard et al., 1994, Eur. J. Biochem. 225:565-572.
Mullen et al., 1994, Plant Physiol., 105:113 (Abstr. 606).
Mulligan, 1993, Science, 260:926-931.
Pachnis et al., 1990, Proc. Natl. Acad. Sci. USA, 87:5109-5113.
Paglia et al., Journal of Experimental Medicine, vol. 183 No. 1, pp. 317-322 (1996).
Peterson et al., 1993, Proc. Natl. Acad. Sci. USA, 90:11207-11211.
Rabinovich et al., 1994, Science, 265:1401-1404.
Sanchez-Pescador et al., 1985, Science, 227:484-492.
Schreuder et al., 1996 Vaccine, 14(5):383-388.
Sousa et al., Journal of Experimental Medicine, vol. 178 No. 2, pp. 509-519 (Aug. 1993).
Stern et al., 1992, Cell, 68:465-477.
Suda et al., 1993, Cell, 75:1169-1178.
Valenzuela et al., 1985 Bio/Technology 3:323-326.
Stubbs et al. "Whole recombinant yeast vaccine activates dendric cells and elicits protective cell-mediated immunity", Nature Medicine May 2001, vol. 7, pp. 1-5.
International Search Report for International (PCT) Patent Application No. PCT/US03/40281, mailed Sep. 22, 2006.
International Preliminary Examination Report for International (PCT) Patent Application No. PCT/US03/40281, mailed Sep. 22, 2006.
Supplementary European Search Report for European Patent Application No. 03814130.5, dated Apr. 24, 2008.
First Office Action for Chinese Patent Application No. 200380109787.5, dated May 23, 2008.
Official Action for U.S. Appl. No. 10/738,646, mailed Jun. 14, 2005.
Official Action for U.S. Appl. No. 10/738,646, mailed Dec. 6, 2005.
Official Action for U.S. Appl. No. 10/738,646, mailed Aug. 29, 2006.
Official Action for U.S. Appl. No. 10/738,646, mailed May 17, 2007.
Official Action for U.S. Appl. No. 10/738,646, mailed Nov. 28, 2007.
Official Action for U.S. Appl. No. 10/738,646, mailed Jul. 1, 2008.
Examiner's First Report for Australian Patent Application No. 2003301021, dated Mar. 12, 2008.
First Examination Report for Indian Patent Application No. 2985/delnp/2005, dated Oct. 12, 2006.
Further Examination Report for Indian Patent Application No. 2985/delnp/2005, dated Sep. 13, 2007.
Translation of Second Office Action for Chinese Patent Application No. 200380109787.5, dated Nov. 28, 2008.
Official Action for U.S. Appl. No. 11/768,144, mailed Oct. 15, 2008.
Childs et al., "Regression of metastatic renal-cell carcinoma after nonmyeloablative allogeneic peripheral-blood stem-cell transplantation," N Engl J Med, Sep. 2000, vol. 343(11), pp. 750-758.
Marshall et al., "Phase I Study of Sequential Vaccinations with Fowlpox-CEA(6D)-TRICOM Alone and Sequentially with Vaccinia-CEA(6D)-TRICOM, with and without Granulocyte-Macrophage Colony-Stimulating Factor, in Patients with Carcinoembryonic Antigen-Expressing Carcinomas," Journal of Clinical Oncology, Feb. 2005, vol. 23(4), pp. 720-731.
Moscatello et al., "A Naturally Occurring Mutant Human Epidermal Growth Factor Receptor as a Target for Peptide Vaccine Immunotherapy of Tumors," Cancer Research, Apr. 1997, vol. 57, pp. 1419-1424.
Schuster et al., "Protein expression in yeast; comparison of two expression strategies regarding protein maturation," Journal of Biotechnology, Dec. 2000, vol. 84, pp. 237-248.
Slavin et al., "Donor lymphocyte infusion: the use of alloreactive and tumor-reactive lymphocytes for immunotherapy of malignant and nonmalignant diseases in conjunction with allogeneic stem cell transplantation," J Hematother Stem Cell Res, Apr. 2002, vol. 11, pp. 265-276.
Zaremba et al., "Identification of an Enhancer Agonist Cytotoxic T Lymphocyte Peptide from Human Carcinoembryonic Antigen," Cancer Research, Oct. 1997, vol. 57, pp. 1570-1577.
Official Action for U.S. Appl. No. 12/334,775, mailed Nov. 12, 2010.
Fenton et al. "Induction of T-Cell Immunity Against Ras Oncoproteins by Soluble Protein or Ras-Expressing *Escherichia coli*," Journal of the National Cancer Institute, Dec. 20, 1995, vol. 87, No. 24, pp. 1853-1861.
Lemoine et al. "High frequency of ras oncogene activation in all stages of human thyroid tumorigenesis." Oncogene, Feb. 1989, vol. 4, No. 2, pp. 159-164 (Abstract only) 1 page.
Official Action for European Patent Application No. 03814130.5, dated Mar. 11, 2011 10 pages.
Official Action for Canada Patent Application No. 2,508,957, dated Mar. 29, 2011 3 pages.
Official Action for U.S. Appl. No. 12/335,094, mailed Feb. 8, 2011 16 pages.
Tannock "Experimental Chemotherapy," The Basic Science of Oncology, Tennock and Hill (eds.) Chapter 19, pp. 338 and 352-359, New York, 1992.
Velders et al. Defined Flanking Spacers and Enhanced Proteolysts is Essential for Eradication of Estabiished Tumors by an Epitope String DNA Vaccine, The Journal of Immunotogy, May 1, 2001, vol. 166, No. 9, pp. 5366-5373.
Yu et al. Vaccination of Malignant Glioma Patients with Peptide-pulsed Dendritic Cells Elicits Systemic Cytotoxicity and Intracranial T-cell Infiltration, Cancer Research, Feb. 2. 2001, vol. 61, pp. 842-847.
Notice of Allowance with English translation for China Patent Application No. 200380109787.5, issued Aug. 31, 2011 4 pages.
Examiner's Report for Australia Patent Application No. 2009208045, dated Sep. 16, 2011 2 pages.
Official Action for U.S. Appl. No. 12/335,094, mailed Jun. 16, 2011 12 pages.
Official Action for U.S. Appl. No. 12/334,775, mailed Jun. 27, 2011 20 pages.
Notice of Aitowance for U.S. Appl. No. 12/335,094, mailed Sep. 12, 2011 5 pages.
Office Action for U.S. Appl. No. 12/643,869, mailed Sep. 22, 2011 12 pages.
Abrams et al., "Mutant ras Epitopes as Targets for Cancer Vaccines", Feb. 1996, vol. 23, abstract only.
Bos, "ras Oncogenes in Human Cancer: A Review", Cancer Research, Sep. 1, 1989, vol. 49, pp. 4682-4689.
Chen et al., "Comparison of the Average Structures, from Molecular Dynamics, of Complexes of GTPase Activating Protein (GAP) with Oncogenic and Wild-Type ras-p21: Identification of Potential Effector Domains", Journal of Protein D Chemistry, Jul. 2002, vol. 21, pp. 349-359.

Downward, "Targeting Ras Signalling Pathways in Cancer Therapy", Nature Reviews, Jan. 2003, vol. 3, pp. 11-22.

Eto et al., "Immunization with recombinant *Escherichia coli* expressing retinal S-antigen-induced experimental autoimmune uveitis (EAU) in Lewis rats", Cellular Immunology, vol. 147, No. 1 Mar. 1993, pp. 203-214.

Huncharek et al., "K-ras as a Prognostic Marker in Non-small Cell Lung Cancer: a Combined Analysis of 881 Cases", Carcinogenesis, 1999, vol. 20, pp. 1507-1510.

Klepfer et al., Archives of Virology, 1993, vol. 128, pp. 269-286.

Midgley and Kerr, "Ras as a Target in Cancer Therapy", Critical Reviews in Oncology/Hematology, 2002, vol. 44, pp. 109-112.

Nielsen et al., "Sensitivity of Wild Type and Mutant ras Alleles to Ras Specific Exchange Factors: Identification of Factor Specific Requirements", Oncogene, 2001, vol. 20, pp. 2091-2100.

Schleger et al., "The Role of Wild-Type and Mutated N-ras in the Malignant Transformation of Liver Cells", Molecular Carcinogenesis, 2000, vol. 28, pp. 31-41.

Sinai et al., "Enhancement of Resistance to Infectious Diseases by Oral Administration of Brewer's Yeast," Infection and Immunity, vol. 9 No. 5, pp. 781-787 (May 1974).

Wittinghofer et al., "Three-Dimensional Structure of p21 in the Active Conformation and Analysis of an Oncogenic Mutant", Environmental Health Perspectives, 1991, vol. 93, pp. 11-15.

Wu, Database DISSABS, on STN, AN 2001:14790, "Structural Analysis of Oncogenic H-ras Mutants G12A and G13A", Masters Abstract International, 1999, vol. 38, p. 954, abstract.

Notice of Allowance for U.S. Appl. No. 11/768,144, mailed May 7, 2009.

Notice of Acceptance for Australian Patent Application No. 2003301021, maield Apr. 23, 2009.

Official Action for Canadian Patent Application No. 2,508,957, dated Oct. 13, 2009.

Translation of Decision of Final Rejection of the Application for Chinese Patent Application No. 200380109787.5, issuing date Mar. 18, 2010.

Notificaion of Reasons for Refusal (including translation) for Japanese Patent Application No. 2004-563714, mailed Feb. 16, 2010.

\* cited by examiner

YEAST-BASED VACCINES AS IMMUNOTHERAPY

CROSS-REFERENCE TO RELATED APPLICATIONS

This application is a continuation of U.S. patent application Ser. No. 10/738,646, filed Dec. 16, 2003, now U.S. Pat. No. 7,465,454, which claims the benefit of priority under 35 U.S.C. §119(e) from U.S. Provisional Application Ser. No. 60/434,163, filed Dec. 16, 2002, and entitled "Yeast-Based Vaccines as Cancer Immunotherapy". The entire disclosure of each of U.S. Provisional Application Ser. No. 60/434,163 and U.S. patent application Ser. No. 10/738,646 is incorporated herein by reference.

GOVERNMENT RIGHTS

This invention was supported in part with funding provided by NIH NCI Grant No. P50 CA058187, awarded by the National Institutes of Health. The government has certain rights to this invention.

REFERENCE TO SEQUENCE LISTING

This application contains a Sequence Listing submitted electronically as a text file by EFS-Web. The text file, named "3923-6-2_ST25", has a size in bytes of 35 KB, and was recorded on 5 Dec. 2008. The information contained in the text file is incorporated herein by reference in its entirety pursuant to 37 CFR §1.52(e)(5).

FIELD OF THE INVENTION

The present invention generally relates to the use of yeast-based vaccines comprising heterologous antigens for the elicitation of humoral and cellular immunity and in one aspect, for the prevention and treatment of a variety of cancers in an animal.

BACKGROUND OF THE INVENTION

Neoplasia, or a process of rapid cellular proliferation resulting in new, abnormal growth, is a characteristic of many diseases which can be serious, and sometimes, life-threatening. Typically, neoplastic growth of cells and tissues is characterized by greater than normal proliferation of cells, wherein the cells continue to grow even after the instigating factor (e.g., tumor promoter, carcinogen, virus) is no longer present. The cellular growth tends to show a lack of structural organization and/or coordination with the normal tissue and usually creates a mass of tissue (e.g., a tumor) which may be benign or malignant. Malignant cellular growth, or malignant tumors, are a leading cause of death worldwide, and the development of effective therapy for neoplastic disease is the subject of a large body of research. Although a variety of innovative approaches to treat and prevent cancers have been proposed, many cancers continue to have a high rate of mortality and may be difficult to treat or relatively unresponsive to conventional therapies.

For example, lung cancer is the second most common form of cancer in the United States. It accounts for 15% of all cancers and 28% of all cancer deaths. In 2002 an estimated 177,000 new cases will be diagnosed and 166,000 will die, a mortality rate higher than colorectal, prostate and breast combined. 80% of primary lung tumors are non-small cell lung carcinoma (NSCLC). Standard chemotherapy continues to be relatively ineffective with multiple drug therapy yielding minimal survival advantage with significant toxicity.

As another example, glioblastoma multiforme (glioma) is the most common primary malignant brain tumor in adults. Despite the use of surgery, radiotherapy and chemotherapy, cure rates and median patient survival have not improved. Other tumors also metastasize to the brain and in this setting they respond less well to peripheral chemotherapy due to constraints on drug delivery imposed by the blood/brain barrier. Clearly, more brain tumor-directed therapeutic approaches are needed. One such approach involves immunotherapy. It has been known for some time that lymphocytes primed in the periphery can traverse the blood brain barrier and target brain tissue. Prime targets for brain tumor immunotherapy are vaccines that elicit immune responses against new or mutated antigens expressed specifically in brain tumor cells. The goal then is to provide a vaccine approach that would provide broad, vigorous and long-lasting immune protection against intracranial tumors.

Vaccines are widely used to prevent disease and to treat established diseases (immunotherapeutic vaccines). Protein antigens (e.g. subunit vaccines, the development of which was made possible by recombinant DNA technology), when administered without adjuvants, induce weak humoral (antibody) immunity and have therefore been disappointing to date as they generate only limited immunogenicity. An additional disadvantage of subunit vaccines, as well as of killed virus and recombinant live virus vaccines, is that while they appear to stimulate a strong humoral immune response when administered with adjuvants, they fail to elicit protective cellular immunity. Adjuvants are used experimentally to stimulate potent immune responses in mice, and are desirable for use in human vaccines, but few are approved for human use. Indeed, the only adjuvants approved for use in the United States are the aluminum salts, aluminum hydroxide and aluminum phosphate, neither of which stimulates cell-mediated immunity. Aluminum salt formulations cannot be frozen or lyophilized, and such adjuvants are not effective with all antigens. Moreover, most adjuvants do not lead to induction of cytotoxic T lymphocytes (CTL). CTL are needed to kill cells that are synthesizing aberrant proteins including viral proteins and mutated "self" proteins. Vaccines that stimulate CTL are being intensely studied for use against a variety of diseases, including all cancers (e.g., melanoma, prostate, ovarian, etc.). Thus adjuvants are needed that stimulate CTL and cell-mediated immunity in general.

Yeast have been used in the production of subunit protein vaccines; however, in this case, yeast are used to produce the protein, but the yeast cells or subcellular fractions thereof are not actually delivered to the patient. Yeast have also been fed to animals prior to immunization to try to prime the immune response in a non-specific manner (i.e., to stimulate phagocytosis as well as the production of complement and interferon). The results have been ambiguous, and such protocols have not generated protective cellular immunity; see, for example, Fattal-German et al., 1992, *Dev. Biol. Stand.* 77, 115-120; Bizzini et al., 1990, *FEMS Microbiol. Immunol.* 2, 155-167.

U.S. Pat. No. 5,830,463, issued Nov. 3, 1998, to Duke et al. described the use of nonpathogenic yeast carrying at least one compound capable of modulating an immune response, and demonstrated that such complexes are efficacious at stimulating cell-mediated, as well as humoral, immunity. In particular, U.S. Pat. No. 5,830,463 demonstrated that yeast which are genetically engineered to express a heterologous antigen can elicit both a cell-mediated and a humoral immune response when administered to an animal.

Despite the current advances in cancer therapy and vaccine technology, there remains an urgent need to develop safe and effective vaccines and adjuvants for diseases that are amenable to immunotherapy, including disease caused by neoplastic transformation (cancer), and particularly, for those cancers that are especially resistant to treatment using conventional cancer therapy and generic vaccine strategies.

SUMMARY OF THE INVENTION

One embodiment of the present invention relates to a method to protect an animal against a cancer, comprising administering to an animal that has or is at risk of developing a cancer, a vaccine to reduce or prevent at least one symptom of the cancer in the animal. The vaccine comprises: (a) a yeast vehicle; and (b) a fusion protein expressed by the yeast vehicle, the fusion protein comprising: (i) at least one cancer antigen; and (ii) a peptide linked to the N-terminus of the cancer antigen, the peptide consisting of at least two amino acid residues that are heterologous to the cancer antigen, wherein the peptide stabilizes the expression of the fusion protein in the yeast vehicle or prevents posttranslational modification of the expressed fusion protein. The fusion protein has the following additional requirements: (1) the amino acid residue at position one of the fusion protein is a methionine; (2) the amino acid residue at position two of the fusion protein is not a glycine or a proline; (3) none of the amino acid residues at positions 2-6 of the fusion protein is a methionine; and, (4) none of the amino acid residues at positions 2-5 of the fusion protein is a lysine or an arginine. In one aspect, the peptide consists of at least 2-6 amino acid residues that are heterologous to the cancer antigen. In another aspect, the peptide comprises an amino acid sequence of $M-X_2-X_3-X_4-X_5-X_6$, wherein $X_2$ is any amino acid except glycine, proline, lysine or arginine; wherein $X_3$ is any amino acid except methionine, lysine or arginine; wherein $X_4$ is any amino acid except methionine, lysine or arginine; wherein $X_5$ is any amino acid except methionine, lysine or arginine; and wherein $X_6$ is any amino acid except methionine. In one aspect, $X_6$ is a proline. In another aspect, the peptide comprises an amino acid sequence of M-A-D-E-A-P (SEQ ID NO:1).

Another embodiment of the present invention relates to a method to protect an animal against a cancer, comprising administering to an animal that has or is at risk of developing a cancer, a vaccine to reduce or prevent at least one symptom of the cancer in the animal. The vaccine comprises: (a) a yeast vehicle; and (b) a fusion protein expressed by the yeast vehicle, the fusion protein comprising: (i) at least one cancer antigen; and (ii) a yeast protein linked to the N-terminus of the cancer antigen, wherein the yeast protein consists of between about two and about 200 amino acids of an endogenous yeast protein, wherein the yeast protein stabilizes the expression of the fusion protein in the yeast vehicle or prevents posttranslational modification of the expressed fusion protein. In one aspect, the yeast protein comprises an antibody epitope for identification and purification of the fusion protein.

In either of the above-described embodiments of the invention, the following additional aspects are contemplated. In one aspect, the fusion protein comprises at least two or more cancer antigens. In another aspect, the fusion protein comprises at least one or more immunogenic domain of one or more cancer antigens. In another aspect, the cancer antigen is an antigen associated with a cancer selected from the group consisting of: melanomas, squamous cell carcinoma, breast cancers, head and neck carcinomas, thyroid carcinomas, soft tissue sarcomas, bone sarcomas, testicular cancers, prostatic cancers, ovarian cancers, bladder cancers, skin cancers, brain cancers, angiosarcomas, hemangiosarcomas, mast cell tumors, primary hepatic cancers, lung cancers, pancreatic cancers, gastrointestinal cancers, renal cell carcinomas, hematopoietic neoplasias and metastatic cancers thereof.

In yet another aspect, the cancer antigen is wild-type or mutant protein encoded by a ras gene. For example, the cancer antigen can include a wild-type or mutant protein encoded by a ras gene selected from the group consisting of: K-ras, N-ras and H-ras genes. In one aspect, the ras gene encodes a Ras protein with single or multiple mutations. In another aspect, the cancer antigen comprises fragments of at least 5-9 contiguous amino acid residues of a wild-type Ras protein containing amino acid positions 12, 13, 59 or 61 relative to the wild-type Ras protein, wherein the amino acid residues at positions 12, 13, 59 or 61 are mutated with respect to the wild-type Ras protein.

In yet another aspect, the cancer antigen consists of a fusion protein construct comprising multiple domains, wherein each domain consists of a peptide from an oncoprotein, the peptide consisting of at least 4 amino acid residues flanking either side of and including a mutated amino acid that is found in the protein, wherein the mutation is associated with tumorigenicity. In this aspect, the fusion protein construct consists of at least one peptide that is fused in frame with another mutated tumor antigen, wherein the peptide is selected from the group consisting of: (a) a peptide comprising at least from positions 8-16 of SEQ ID NO:3, wherein the amino acid residue at position 12 with respect to SEQ ID NO:3 is mutated as compared to SEQ ID NO:3; (b) a peptide comprising at least from positions 9-17 of SEQ ID NO:3, wherein the amino acid residue at position 13 with respect to SEQ ID NO:3 is mutated as compared to SEQ ID NO:3; (c) a peptide comprising at least from positions 55-63 of SEQ ID NO:3, wherein the amino acid residue at position 59 with respect to SEQ ID NO:3 is mutated as compared to SEQ ID NO:3; and (d) a peptide comprising at least from positions 57-65 of SEQ ID NO:3, wherein the amino acid residue at position 61 with respect to SEQ ID NO:3 is mutated as compared to SEQ ID NO:3. In one aspect, the mutated tumor antigen is a Ras protein comprising at least one mutation relative to a wild-type Ras protein sequence.

In one embodiment of either of the above-identified methods, the vaccine is administered to the respiratory tract. In another embodiment, the vaccine is administered by a parenteral route of administration. In yet another embodiment, the vaccine further comprises dendritic cells or macrophages, wherein the yeast vehicle expressing the fusion protein is delivered to dendritic cells or macrophages ex vivo and wherein the dendritic cell or macrophage containing the yeast vehicle expressing the cancer antigen is administered to the animal. In one aspect of this embodiment, the dendritic cell or the yeast vehicle has been additionally loaded with free antigen. In one aspect, the vaccine is administered as a therapeutic vaccine. In another aspect, the vaccine is administered as a prophylactic vaccine. In one aspect, the animal has or is at risk of developing a cancer selected from the group consisting of brain cancer, lung cancer, breast cancer, melanoma, and renal cancer. In another aspect, the animal has cancer and wherein administration of the vaccine occurs after surgical resection of a tumor from the animal. In yet another aspect, the animal has cancer and wherein administration of the vaccine occurs after surgical resection of a tumor from the animal and after administration of non-myeloablative allogeneic stem cell transplantation. In yet another aspect, the animal has cancer and wherein administration of the vaccine occurs after surgical resection of a tumor from the animal, after administration of non-myeloablative allogeneic stem cell transplantation, and after allogeneic donor lymphocyte infusion.

Another embodiment of the invention relates to a method to protect an animal against a brain cancer or a lung cancer, comprising administering to the respiratory tract of an animal that has or is at risk of developing a brain cancer or a lung cancer, a vaccine comprising a yeast vehicle and at least one cancer antigen, to reduce or prevent at least one symptom of the brain cancer or lung cancer in the animal. In this embodiment, the vaccine can include any of the above-described fusion proteins, as well as other antigens. In one aspect, the vaccine comprises at least two or more cancer antigens. In another aspect, the cancer antigen is a fusion protein comprising at least one or more cancer antigens. In yet another aspect, the cancer antigen is a fusion protein comprising at least one or more immunogenic domains of one or more cancer antigens.

In one aspect of this embodiment, the vaccine is administered by intranasal administration. In another aspect, the vaccine is administered by intratracheal administration. In yet another embodiment, the yeast vehicle and the cancer antigen are delivered to dendritic cells or macrophages ex vivo and wherein the dendritic cell or macrophage containing the yeast vehicle and cancer antigen are administered to the respiratory tract of the animal.

In one aspect, the method protects the animal against a brain cancer, including, but not limited to a primary brain cancer, such as a glioblastoma multiforme, or a metastatic cancer from a different organ. In another embodiment, the method protects the animal against a lung cancer, including, but not limited to a primary lung cancer (e.g., non-small cell carcinomas, small cell carcinomas and adenocarcinomas) or a metastatic cancer from a different organ. In one aspect, the vaccine is administered as a therapeutic vaccine. In another aspect, the vaccine is administered as a prophylactic vaccine.

Yet another embodiment of the present invention relates to a method to elicit an antigen-specific humoral immune response and an antigen-specific cell-mediated immune response in an animal. The method includes administering to the animal a therapeutic composition comprising: (a) a yeast vehicle; and (b) a fusion protein expressed by the yeast vehicle, the fusion protein comprising: (i) at least one antigen; and (ii) a peptide linked to the N-terminus of the antigen, the peptide consisting of at least two amino acid residues that are heterologous to the antigen, wherein the peptide stabilizes the expression of the fusion protein in the yeast vehicle or prevents posttranslational modification of the expressed fusion protein. The fusion protein has the following additional requirements: the amino acid residue at position one of the fusion protein is a methionine; the amino acid residue at position two of the fusion protein is not a glycine or a proline; none of the amino acid residues at positions 2-6 of the fusion protein is a methionine; and, none of the amino acid residues at positions 2-5 of the fusion protein is a lysine or an arginine. In one aspect, the peptide consists of at least six amino acid residues that are heterologous to the antigen. In another aspect, the peptide comprises an amino acid sequence of M-$X_2$-$X_3$-$X_4$-$X_5$-$X_6$: wherein $X_2$ is any amino acid except glycine, proline, lysine or arginine; wherein $X_3$ is any amino acid except methionine, lysine or arginine; wherein $X_4$ is any amino acid except methionine, lysine or arginine; wherein $X_5$ is any amino acid except methionine, lysine or arginine; and wherein $X_6$ is any amino acid except methionine. In one aspect, $X_6$ is a proline. In one aspect, the peptide comprises an amino acid sequence of M-A-D-E-A-P (SEQ ID NO:1). In one aspect, the antigen is selected from the group consisting of: a viral antigen, an overexpressed mammalian cell surface molecule, a bacterial antigen, a fungal antigen, a protozoan antigen, a helminth antigen, an ectoparasite antigen, a cancer antigen, a mammalian cell molecule harboring one or more mutated amino acids, a protein normally expressed pre- or neo-natally by mammalian cells, a protein whose expression is induced by insertion of an epidemiologic agent (e.g. virus), a protein whose expression is induced by gene translocation, and a protein whose expression is induced by mutation of regulatory sequences.

Another embodiment relates to a vaccine as described for use in the method above.

Yet another embodiment of the invention relates to a method to elicit an antigen-specific humoral immune response and an antigen-specific cell-mediated immune response in an animal. The method includes administering to the animal a therapeutic composition comprising: (a) a yeast vehicle; and (b) a fusion protein expressed by the yeast vehicle, the fusion protein comprising: (i) at least one antigen; and (ii) a yeast protein linked to the N-terminus of the antigen, wherein the yeast protein consists of between about two and about 200 amino acids of an endogenous yeast protein, wherein the yeast protein stabilizes the expression of the fusion protein in the yeast vehicle or prevents posttranslational modification of the expressed fusion protein. In one aspect, the yeast protein comprises an antibody epitope for identification and purification of the fusion protein.

Another embodiment of the invention is a vaccine as described for use in the method above.

Yet another embodiment of the present invention relates to a method treat a patient that has cancer, comprising: (a) treating a patient that has cancer by nonmyeloablative stem cell transfer effective to establish a stable mixed bone marrow chimerism, wherein the stem cells are provided by an allogeneic donor; (b) administering lymphocytes obtained from the allogeneic donor to the patient; and (c) administering to the patient, after step (b), a vaccine comprising a yeast vehicle and at least one cancer antigen. In one aspect, the method also includes administering to the allogeneic donor, prior to step (a), a vaccine comprising a yeast vehicle and at least one cancer antigen. In another embodiment, the method includes removing a tumor from the patient prior to performing step (a).

In one aspect of this method, the vaccine comprises at least two or more cancer antigens. In another aspect, the cancer antigen is a fusion protein comprising one or more cancer antigens. In yet another aspect, the cancer antigen is a fusion protein comprising one or more immunogenic domains of one or more cancer antigens. In another aspect, the cancer antigen consists of a fusion protein construct comprising multiple domains, wherein each domain consists of a peptide from an oncoprotein, the peptide consisting of at least 4 amino acid residues flanking either side of and including a mutated amino acid that is found in the protein, wherein the mutation is associated with tumorigenicity. In another aspect, the yeast vehicle expresses the cancer antigen, and wherein the cancer antigen is a fusion protein comprising: (a) at least one cancer antigen; and (b) a peptide linked to the N-terminus of the cancer antigen, the peptide consisting of at least two amino acid residues that are heterologous to the cancer antigen, wherein the peptide stabilizes the expression of the fusion protein in the yeast vehicle or prevents posttranslational modification of the expressed fusion protein: wherein the amino acid residue at position one of the fusion protein is a methionine; wherein the amino acid residue at position two of the fusion protein is not a glycine or a proline; wherein none of the amino acid residues at positions 2-6 of the fusion protein is a methionine; and, wherein none of the amino acid residues at positions 2-5 of the fusion protein is a lysine or an arginine. In another aspect, the yeast vehicle expresses the cancer antigen, and wherein the cancer antigen is a fusion protein comprising: (a) at least one cancer antigen; and (b) a yeast protein linked to the N-terminus of the cancer antigen, wherein the yeast protein consists of between about two and about 200 amino acids of an endogenous yeast protein, wherein the yeast protein stabilizes the expression of the fusion protein in the yeast vehicle or prevents posttranslational modification of the expressed fusion protein.

In one aspect of this embodiment, the vaccine is administered by intranasal administration. In another aspect, the vaccine is administered by parenteral administration. In another aspect, the yeast vehicle and the cancer antigen are delivered to dendritic cells or macrophages ex vivo and wherein the dendritic cell or macrophage containing the yeast vehicle and cancer antigen are administered to the respiratory tract of the animal.

In any of the above-described methods and compositions of the present invention, the following aspects related to the yeast vehicle are included in the invention. In one embodiment, yeast vehicle is selected from the group consisting of a whole yeast, a yeast spheroplast, a yeast cytoplast, a yeast ghost, and a subcellular yeast membrane extract or fraction thereof. In one aspect, a yeast cell or yeast spheroplast used to prepare the yeast vehicle was transformed with a recombinant nucleic acid molecule encoding the antigen such that the antigen is recombinantly expressed by the yeast cell or yeast spheroplast. In this aspect, the yeast cell or yeast spheroplast that recombinantly expresses the antigen is used to produce a yeast vehicle comprising a yeast cytoplast, a yeast ghost, or a subcellular yeast membrane extract or fraction thereof. In one aspect, the yeast vehicle is from a non-pathogenic yeast. In another aspect, the yeast vehicle is from a yeast selected from the group consisting of: *Saccharomyces*, *Schizosaccharomyces*, *Kluveromyces*, *Hansenula*, *Candida* and *Pichia*. In one aspect, the *Saccharomyces* is *S. cerevisiae*.

In general, the yeast vehicle and antigen can be associated by any technique described herein. In one aspect, the yeast vehicle was loaded intracellularly with the cancer antigen. In another aspect, the cancer antigen was covalently or non-covalently attached to the yeast vehicle. In yet another aspect, the yeast vehicle and the cancer antigen were associated by mixing. In another aspect, the antigen is expressed recombinantly by the yeast vehicle or by the yeast cell or yeast spheroplast from which the yeast vehicle was derived.

BRIEF DESCRIPTION OF THE DRAWINGS OF THE INVENTION

DETAILED DESCRIPTION OF THE INVENTION

Figure 1:
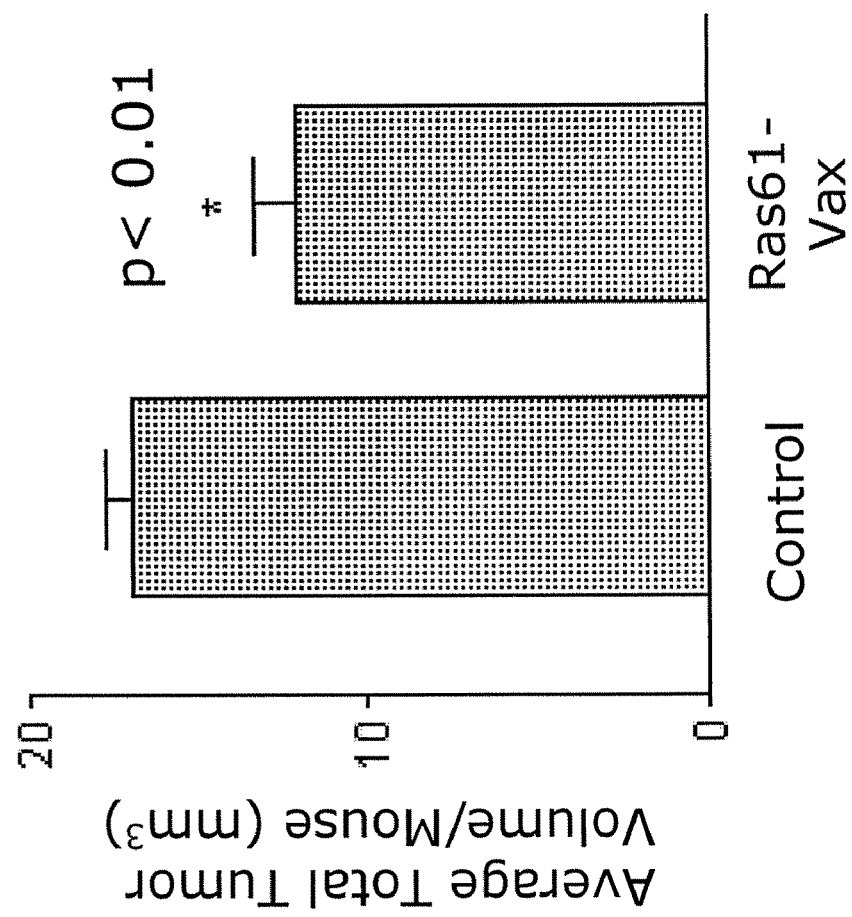
FIG. 1 is a bar graph showing that the yeast-based Ras61-VAX vaccine controls preexisting, urethane-induced lung tumors in vivo.

The present invention generally relates to compositions and methods for treating and/or preventing a variety of diseases and conditions that are amenable to immunotherapy and, in one particular embodiment, to compositions and methods for treating and/or preventing cancer in an animal. The invention includes the use of a yeast-based vaccine comprising a yeast vehicle and an antigen that is selected to elicit an antigen-specific cellular and humoral immune response in an animal, for use in prophylactic and/or therapeutic vaccination and the prevention and/or treatment of a variety of diseases and conditions. In particular, the inventors describe herein the use of yeast-based vaccines to reduce tumors in a variety of different forms of cancer in vivo, including lung cancer, brain cancer, breast cancer, and renal cancer. Also described herein are improvements to a yeast-based vaccine that are applicable not only to cancer therapies, but to the treatment of a variety of immunotherapeutic methods and compositions.

The inventors have previously described a vaccine technology that elicits potent cell-mediated immunity, including cytotoxic T cell (CTL) responses. The vaccine technology involves using yeast and derivatives thereof as a vaccine vector, wherein the yeast are engineered to express or are otherwise loaded with relevant antigen(s) to elicit an immune response against the antigen(s). This technology is generally described in U.S. Pat. No. 5,830,463 and is incorporated herein by reference in its entirety. The present invention takes the existing yeast vaccine technology described in U.S. Pat. No. 5,830,463 and provides specific improvements in a method to reduce cancer using yeast vehicles and selected cancer antigens, as well as new yeast vaccines comprising novel proteins that have enhanced stability, and methods of using the new yeast vaccines to treat any disease or condition for which elicitation of an immune response may have a therapeutic benefit. A general description of yeast vaccines that can be used in various embodiments of the invention is also described in copending U.S. application Ser. No. 09/991,363, which is incorporated by reference in its entirety.

In particular, the present inventors have discovered that, while multiple routes of immunization may be equivalently effective for destroying tumors in the periphery, the yeast-based vaccine used in the present invention is able to prime effector cells that may be unique to the lung. Therefore, although other routes of administration are still effective, administration of the yeast vaccines through the respiratory tract (e.g., intranasal, inhaled, intratracheal) provides a surprisingly robust immune response and anti-tumor effect that is not achieved using other routes of administration investigated thus far. In particular, the present inventors have discovered that administration of the yeast vaccine to the respiratory tract is significantly better at reducing tumors in lung cancer than when the vaccine is administered to the periphery. Perhaps even more surprising was the result that in brain tumors, while administration of the yeast vaccine to the respiratory tract induced a potent anti-tumor response in all experimental models examined thus far, peripheral administration of the vaccine (subcutaneous) was less effective at inducing an anti-tumor response in the brain, and in at least one experimental model for brain cancer, peripheral administration failed to provide a significant anti-tumor effect in the brain. Therefore, yeast-based vaccines of the present invention can prime unique immune effector cell precursors in the lungs, and such immune cells may be particularly effective for crossing the blood-brain barrier to influence the course of intracranial tumor growth. Without being bound by theory, the present inventors believe that the route of immunization may be an important component in the design of an effective vaccine for at least brain tumors and lung tumors. Because the yeast-based vaccine of the invention is extremely facile for multiple routes of immunization, the vaccine holds the promise to uniquely provoke highly specialized immune responses with heretofore underappreciated potential for the treatment of some cancers.

The present inventors have also discovered that the use of the yeast vaccines of the present invention in a novel modification of a mixed allogeneic bone marrow chimera protocol previously described by Luznik et al. (*Blood* 101 (4): 1645-1652, 2003; incorporated herein by reference in its entirety) results in excellent induction of therapeutic immunity and anti-tumor responses in vivo. Significantly, this result can be achieved without the need to use whole tumor preparations from the recipient and without the need to enhance the vaccine with biological response modifiers, such as granulocyte-macrophage colony-stimulating factor (GM-CSF), and without the need for the use of conventional adjuvants. In addition, the use of the yeast vehicle of the present invention provides extreme flexibility in the choice of the antigen and antigen combinations, and provides significant enhancements of cellular immunity against the antigen. Moreover, the present invention provides additional enhancement of the protocol by providing for the immunization of the donor with the yeast vaccine of the invention in a controlled, selective manner.

In addition, the present inventors have developed improvements to the yeast-based vaccine technology using novel fusion proteins that stabilize the expression of the heterologous protein in the yeast vehicle and/or prevent posttranslational modification of the expressed heterologous protein. Specifically, the inventors describe herein a novel construct for expression of heterologous antigens in yeast, wherein the desired antigenic protein(s) or peptide(s) are fused at their amino-terminal end to: (a) a synthetic peptide; or (b) at least a portion of an endogenous yeast protein, wherein either fusion partner provides significantly enhanced stability of expression of the protein in the yeast and/or a prevents post-translational modification of the proteins by the yeast cells. Also, the fusion peptides provide an epitope that can be designed to be recognized by a selection agent, such as an antibody, and do not appear to negatively impact the immune response against the vaccinating antigen in the construct. Such agents are useful for the identification, selection and purification of proteins useful in the invention.

In addition, the present invention contemplates the use of peptides that are fused to the C-terminus of the antigen construct, particularly for use in the selection and identification of the protein. Such peptides include, but are not limited to, any synthetic or natural peptide, such as a peptide tag (e.g., 6× His) or any other short epitope tag. Peptides attached to the C-terminus of an antigen according to the invention can be used with or without the addition of the N-terminal peptides discussed above.

Finally, the present inventors describe herein novel fusion protein antigens for use in a yeast-based vaccine that provide multiple immunogenic domains from one or more antigens within the same construct. Such fusion proteins are particularly useful when it is desirable to encompass several different mutations and/or combinations of mutations that may occur at one or a few positions in the antigen in nature, in a single vaccine construct. For example, it is known that there are several different mutations in the oncogenes of the ras gene family that can be associated with a tumor cell phenotype in nature. Mutations at the codon encoding amino acid 12 in the Ras protein are found in 78% of pancreatic cancers, 34% of colorectal cancers, 27% of non-small cell lung carcinomas, and 24% of ovarian cancers. Different mutations at positions 13, 59 and 61 are also found in a variety of cancers. Using the yeast-based vaccine approach, the present inventors describe herein the production of fusion proteins, including, but not limited to, fusion proteins based on ras mutations, that can capture several mutations at the same position and/or different combinations of mutations at more than one position, all within the same antigen vaccine.

As a general description of the methods and compositions used in the present invention, the vaccine and methods described herein integrate efficient antigen delivery with extremely effective T cell activation in a powerful vaccine formulation that does not require accessory adjuvant components or biological mediators. The vaccine approach described herein has many other attributes that make it an ideal vaccine candidate, including, but not limited to, ease of construction, low expense of mass production, biological stability, and safety. No grossly adverse effects of immunization with whole yeast were apparent at the time of the initial vaccination or upon repeated administration in either mice, rats, rabbits, pig-tailed macaques (*Macaca nemestrina*), rhesus macaques, or immunodeficient CB. $17^{scid}$ mice (unpublished observations). Moreover, as described in application Ser. No. 09/991,363, supra, the ability of yeast-antigen complexes to mature dendritic cells into potent antigen presenting cells (APCs) while efficiently delivering antigens into both MHC class-I and class-II processing pathways indicates that yeast-based vaccine vectors will provide a powerful strategy for the induction of cell-mediated immunity directed against a variety of infectious diseases and cancer targets. Indeed, the data described herein and the advances for the yeast-based vaccine technology continue to prove this general principle while providing significant improvements to the technology that have not been previously appreciated.

According to the present invention, a yeast vehicle is any yeast cell (e.g., a whole or intact cell) or a derivative thereof (see below) that can be used in conjunction with an antigen in a vaccine or therapeutic composition of the invention, or as an adjuvant. The yeast vehicle can therefore include, but is not limited to, a live intact yeast microorganism (i.e., a yeast cell having all its components including a cell wall), a killed (dead) intact yeast microorganism, or derivatives thereof including: a yeast spheroplast (i.e., a yeast cell lacking a cell wall), a yeast cytoplast (i.e., a yeast cell lacking a cell wall and nucleus), a yeast ghost (i.e., a yeast cell lacking a cell wall, nucleus and cytoplasm), or a subcellular yeast membrane extract or fraction thereof (also referred to previously as a subcellular yeast particle).

Yeast spheroplasts are typically produced by enzymatic digestion of the yeast cell wall. Such a method is described, for example, in Franzusoff et al., 1991, *Meth. Enzymol.* 194, 662-674, incorporated herein by reference in its entirety. Yeast cytoplasts are typically produced by enucleation of yeast cells. Such a method is described, for example, in Coon, 1978, *Natl. Cancer Inst. Monogr.* 48, 45-55 incorporated herein by reference in its entirety. Yeast ghosts are typically produced by resealing a permeabilized or lysed cell and can, but need not, contain at least some of the organelles of that cell. Such a method is described, for example, in Franzusoff et al., 1983, *J. Biol. Chem.* 258, 3608-3614 and Bussey et al., 1979, *Biochim. Biophys. Acta* 553, 185-196, each of which is incorporated herein by reference in its entirety. A subcellular yeast membrane extract or fraction thereof refers to a yeast membrane that lacks a natural nucleus or cytoplasm. The particle can be of any size, including sizes ranging from the size of a natural yeast membrane to microparticles produced by sonication or other membrane disruption methods known to those skilled in the art, followed by resealing. A method for producing subcellular yeast membrane extracts is described, for example, in Franzusoff et al., 1991, *Meth. Enzymol.* 194, 662-674. One may also use fractions of yeast membrane extracts that contain yeast membrane portions and, when the antigen was expressed recombinantly by the yeast prior to preparation of the yeast membrane extract, the antigen of interest.

Any yeast strain can be used to produce a yeast vehicle of the present invention. Yeast are unicellular microorganisms that belong to one of three classes: Ascomycetes, Basidiomycetes and Fungi Imperfecti. While pathogenic yeast strains, or nonpathogenic mutants thereof can be used in accordance with the present invention, nonpathogenic yeast strains are preferred. Preferred genera of yeast strains include *Saccharomyces, Candida* (which can be pathogenic), *Cryptococcus, Hansenula, Kluyveromyces, Pichia, Rhodotorula, Schizosaccharomyces* and *Yarrowia*, with *Saccharomyces, Candida, Hansenula, Pichia* and *Schizosaccharomyces* being more preferred, and with *Saccharomyces* being particularly preferred. Preferred species of yeast strains include *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus* var. *lactis, Pichia pastoris, Rhodotorula rubra, Schizosaccharomyces pombe,* and *Yarrowia lipolytica*. It is to be appreciated that a number of these species include a variety of subspecies, types, subtypes, etc. that are meant to be included within the aforementioned species. More preferred yeast species include *S. cerevisiae, C. albicans, H. polymorpha, P. pastoris* and *S. pombe. S. cerevisiae* is particularly preferred due to it being relatively easy to manipulate and being "Generally Recognized As Safe" or "GRAS" for use as food additives (GRAS, FDA proposed Rule 62FR18938, Apr. 17, 1997). One embodiment of the present invention is a yeast strain that is capable of replicating plasmids to a particularly high copy number, such as a *S. cerevisiae* cir° strain.

In one embodiment, a preferred yeast vehicle of the present invention is capable of fusing with the cell type to which the yeast vehicle and antigen is being delivered, such as a dendritic cell or macrophage, thereby effecting particularly efficient delivery of the yeast vehicle, and in many embodiments, the antigen, to the cell type. As used herein, fusion of a yeast vehicle with a targeted cell type refers to the ability of the yeast cell membrane, or particle thereof, to fuse with the membrane of the targeted cell type (e.g., dendritic cell or macrophage), leading to syncytia formation. As used herein, a syncytium is a multinucleate mass of protoplasm produced by the merging of cells. A number of viral surface proteins (including those of immunodeficiency viruses such as HIV, influenza virus, poliovirus and adenovirus) and other fusogens (such as those involved in fusions between eggs and sperm) have been shown to be able to effect fusion between two membranes (i.e., between viral and mammalian cell membranes or between mammalian cell membranes). For example, a yeast vehicle that produces an HIV gp120/gp41 heterologous antigen on its surface is capable of fusing with a CD4+ T-lymphocyte. It is noted, however, that incorporation of a targeting moiety into the yeast vehicle, while it may be desirable under some circumstances, is not necessary. The present inventors have previously shown that yeast vehicles of the present invention are readily taken up by dendritic cells (as well as other cells, such as macrophages).

Yeast vehicles can be formulated into compositions of the present invention, including preparations to be administered to a patient directly or first loaded into a carrier such as a dendritic cell, using a number of techniques known to those skilled in the art. For example, yeast vehicles can be dried by lyophilization or frozen by exposure to liquid nitrogen or dry ice. Formulations comprising yeast vehicles can also be prepared by packing yeast in a cake or a tablet, such as is done for yeast used in baking or brewing operations. In addition, prior to loading into a dendritic cell, or other type of administration with an antigen, yeast vehicles can also be mixed with a pharmaceutically acceptable excipient, such as an isotonic buffer that is tolerated by the host cell. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, glycerol or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise, for example, dextrose, human serum albumin, and/or preservatives to which sterile water or saline can be added prior to administration.

One component of a therapeutic composition or vaccine of the present invention includes at least one antigen for vaccinating an animal. The composition or vaccine can include, one, two, a few, several or a plurality of antigens, including one or more immunogenic domains of one or more antigens, as desired. According to the present invention, the general use herein of the term "antigen" refers: to any portion of a protein (peptide, partial protein, full-length protein), wherein the protein is naturally occurring or synthetically derived, to a cellular composition (whole cell, cell lysate or disrupted cells), to an organism (whole organism, lysate or disrupted cells) or to a carbohydrate or other molecule, or a portion thereof, wherein the antigen elicits an antigen-specific immune response (humoral and/or cellular immune response), or alternatively acts as a toleragen, against the same or similar antigens that are encountered within the cells and tissues of the animal to which the antigen is administered.

In one embodiment of the present invention, when it is desirable to stimulate an immune response, the term "antigen" can be used interchangeably with the term "immunogen", and is used herein to describe a protein, peptide, cellular composition, organism or other molecule which elicits a humoral and/or cellular immune response (i.e., is antigenic), such that administration of the immunogen to an animal (e.g., via a vaccine of the present invention) mounts an antigen-specific immune response against the same or similar antigens that are encountered within the tissues of the animal.

Therefore, to vaccinate an animal against a particular antigen means, in one embodiment, that an immune response is elicited against the antigen as a result of administration of the antigen. Vaccination preferably results in a protective or therapeutic effect, wherein subsequent exposure to the antigen (or a source of the antigen) elicits an immune response against the antigen (or source) that reduces or prevents a disease or condition in the animal. The concept of vaccination is well known in the art. The immune response that is elicited by administration of a therapeutic composition of the present invention can be any detectable change in any facet of the immune response (e.g., cellular response, humoral response, cytokine production), as compared to in the absence of the administration of the vaccine.

In another embodiment, when it is desirable to suppress an immune response against a given antigen, an antigen can include a toleragen. According to the present invention, a toleragen is used to describe a protein, peptide, cellular composition, organism or other molecule that is provided in a form, amount, or route of administration such that there is a reduced or changed immune response to the antigen, and preferably substantial non-responsiveness, anergy, other inactivation, or deletion of immune system cells in response to contact with the toleragen or a cell expressing or presenting such toleragen.

A "vaccinating antigen" can be an immunogen or a toleragen, but is an antigen used in a vaccine, where a biological response (elicitation of an immune response, tolerance) is to be elicited against the vaccinating antigen.

An immunogenic domain of a given antigen can be any portion of the antigen (i.e., a peptide fragment or subunit) that contains at least one epitope that acts as an immunogen when administered to an animal. For example, a single protein can contain multiple different immunogenic domains.

An epitope is defined herein as a single immunogenic site within a given antigen that is sufficient to elicit an immune response, or a single toleragenic site within a given antigen that is sufficient to suppress, delete or render inactive an immune response. Those of skill in the art will recognize that T cell epitopes are different in size and composition from B cell epitopes, and that epitopes presented through the Class I MHC pathway differ from epitopes presented through the Class II MHC pathway. An antigen can be as small as a single epitope, or larger, and can include multiple epitopes. As such, the size of an antigen can be as small as about 5-12 amino acids (e.g., a peptide) and as large as: a full length protein, including a multimer and fusion proteins, chimeric proteins, whole cells, whole microorganisms, or portions thereof (e.g., lysates of whole cells or extracts of microorganisms). In addition, antigens include carbohydrates, such as those expressed on cancer cells, which can be loaded into a yeast vehicle or into a composition of the invention. It will be appreciated that in some embodiments (i.e., when the antigen is expressed by the yeast vehicle from a recombinant nucleic acid molecule), the antigen is a protein, fusion protein, chimeric protein, or fragment thereof, rather than an entire cell or microorganism. In preferred embodiments, the antigen is selected from the group of a tumor antigen or an antigen of an infectious disease pathogen (i.e., a pathogen antigen). In one embodiment, the antigen is selected from the group of: a viral antigen, an overexpressed mammalian cell surface molecule, a bacterial antigen, a fungal antigen, a protozoan antigen, a helminth antigen, an ectoparasite antigen, a cancer antigen, a mammalian cell molecule harboring one or more mutated amino acids, a protein normally expressed pre- or neo-natally by mammalian cells, a protein whose expression is induced by insertion of an epidemiologic agent (e.g. virus), a protein whose expression is induced by gene translocation, and a protein whose expression is induced by mutation of regulatory sequences.

According to the present invention, an antigen suitable for use in the present composition or vaccine can include two or more immunogenic domains or epitopes from the same antigen, two or more antigens immunogenic domains, or epitopes from the same cell, tissue or organism, or two or more different antigens, immunogenic domains, or epitopes from different cells, tissues or organisms. Preferably, the antigen is heterologous to the yeast strain (i.e., is not protein that is naturally produced by the yeast strain in the absence of genetic or biological manipulation).

One embodiment of the invention relates to several improved proteins for use as antigens in the vaccines of the invention. Specifically, the present invention provides new fusion protein constructs that stabilize the expression of the heterologous protein in the yeast vehicle and/or prevent post-translational modification of the expressed heterologous protein. These fusion proteins are most typically expressed as recombinant proteins by the yeast vehicle (e.g., by an intact yeast or yeast spheroplast, which can optionally be further processed to a yeast cytoplast, yeast ghost, or yeast membrane extract or fraction thereof), although it is an embodiment of the invention that one or much such fusion proteins could be loaded into a yeast vehicle or otherwise complexed or mixed with a yeast vehicle as described above to form a vaccine of the present invention.

One such fusion construct useful in the present invention is a fusion protein that includes: (a) at least one antigen (including immunogenic domains and epitopes of a full-length antigen, as well as various fusion proteins and multiple antigen constructs as described elsewhere herein); and (b) a synthetic peptide. The synthetic peptide is preferably linked to the N-terminus of the cancer antigen. This peptide consists of at least two amino acid residues that are heterologous to the cancer antigen, wherein the peptide stabilizes the expression of the fusion protein in the yeast vehicle or prevents posttranslational modification of the expressed fusion protein. The synthetic peptide and N-terminal portion of the antigen together form a fusion protein that has the following requirements: (1) the amino acid residue at position one of the fusion protein is a methionine (i.e., the first amino acid in the synthetic peptide is a methionine); (2) the amino acid residue at position two of the fusion protein is not a glycine or a proline (i.e., the second amino acid in the synthetic peptide is not a glycine or a proline); (3) none of the amino acid residues at positions 2-6 of the fusion protein is a methionine (i.e., the amino acids at positions 2-6, whether part of the synthetic peptide or the protein, if the synthetic peptide is shorter than 6 amino acids, do not include a methionine); and (4) none of the amino acids at positions 2-5 of the fusion protein is a lysine or an arginine (i.e., the amino acids at positions 2-5, whether part of the synthetic peptide or the protein, if the synthetic peptide is shorter than 5 amino acids, do not include a lysine or an arginine). The synthetic peptide can be as short as two amino acids, but is more preferably at least 2-6 amino acids (including 3, 4, 5 amino acids), and can be longer than 6 amino acids, in whole integers, up to about 200 amino acids.

In one embodiment, the peptide comprises an amino acid sequence of $M-X_2-X_3-X_4-X_5-X_6$, wherein M is methionine; wherein $X_2$ is any amino acid except glycine, proline, lysine or arginine; wherein $X_3$ is any amino acid except methionine, lysine or arginine; wherein $X_4$ is any amino acid except methionine, lysine or arginine; wherein $X_5$ is any amino acid except methionine, lysine or arginine; and wherein $X_6$ is any amino acid except methionine. In one embodiment, the $X_6$ residue is a proline. An exemplary synthetic sequence that enhances the stability of expression of an antigen in a yeast cell and/or prevents post-translational modification of the protein in the yeast includes the sequence M-A-D-E-A-P (SEQ ID NO:1). In addition to the enhanced stability of the expression product, the present inventors believe that this fusion partner does not appear to negatively impact the immune response against the vaccinating antigen in the construct. In addition, the synthetic fusion peptides can be designed to provide an epitope that can be recognized by a selection agent, such as an antibody.

According to the present invention, "heterologous amino acids" are a sequence of amino acids that are not naturally found (i.e., not found in nature, in vivo) flanking the specified amino acid sequence, or that are not related to the function of the specified amino acid sequence, or that would not be encoded by the nucleotides that flank the naturally occurring nucleic acid sequence encoding the specified amino acid sequence as it occurs in the gene, if such nucleotides in the naturally occurring sequence were translated using standard codon usage for the organism from which the given amino acid sequence is derived. Therefore, at least two amino acid residues that are heterologous to the cancer antigen are any two amino acid residues that are not naturally found flanking the cancer antigen.

Another embodiment of the present invention relates to a fusion protein that includes: (a) at least one antigen (including immunogenic domains and epitopes of a full-length antigen, as well as various fusion proteins and multiple antigen constructs as described elsewhere herein) that is fused to (b) at least a portion of an endogenous yeast protein. The endogenous yeast protein is preferably fused to the N-terminal end of the cancer antigen(s) and provides significantly enhanced stability of expression of the protein in the yeast and/or a prevents post-translational modification of the proteins by the yeast cells. In addition, the endogenous yeast antigen, as with the synthetic peptide, this fusion partner does not appear to negatively impact the immune response against the vaccinating antigen in the construct. Antibodies may already be available that selectively bind to the endogenous antigen or can be readily generated. Finally, if it is desired to direct a protein to a particular cellular location (e.g., into the secretory pathway, into mitochondria, into the nucleus), then the construct can use the endogenous signals for the yeast protein to be sure that the cellular machinery is optimized for that delivery system.

The endogenous yeast protein consists of between about two and about 200 amino acids (or 22 kDa maximum) of an endogenous yeast protein, wherein the yeast protein stabilizes the expression of the fusion protein in the yeast vehicle or prevents posttranslational modification of the expressed fusion protein. Any suitable endogenous yeast protein can be used in this embodiment, and particularly preferred proteins include, but are not limited to, SUC2 (yeast invertase; which is a good candidate for being able to express a protein both cytosolically and directing it into the secretory pathway from the same promoter, but is dependent on the carbon source in the medium); alpha factor signal leader sequence; SEC7; CPY; phosphoenolpyruvate carboxykinase PCK1, phosphoglycerokinase PGK and triose phosphate isomerase TPI gene products for their repressible expression in glucose and cytosolic localization; Cwp2p for its localization and retention in the cell wall; the heat shock proteins SSA1, SSA3, SSA4, SSC1 and KAR2, whose expression is induced and whose proteins are more thermostable upon exposure of cells to heat treatment; the mitochondrial protein CYC1 for import into mitochondria; BUD genes for localization at the yeast cell bud during the initial phase of daughter cell formation; ACT1 for anchoring onto actin bundles.

In one embodiment, the endogenous yeast protein/peptide or the synthetic peptide comprises an antibody epitope for identification and purification of the fusion protein. Preferably, an antibody is available or produced that selectively binds to the fusion partner. According to the present invention, the phrase "selectively binds to" refers to the ability of an antibody, antigen binding fragment or binding partner of the present invention to preferentially bind to specified proteins. More specifically, the phrase "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen binding fragment thereof in the absence of the antigen is considered to be background. Binding can be measured using a variety of methods standard in the art including enzyme immunoassays (e.g., ELISA), immunoblot assays, etc.).

Antibodies are characterized in that they comprise immunoglobulin domains and as such, they are members of the immunoglobulin superfamily of proteins. Isolated antibodies of the present invention can include serum containing such antibodies, or antibodies that have been purified to varying degrees. Whole antibodies of the present invention can be polyclonal or monoclonal. Alternatively, functional equivalents of whole antibodies, such as antigen binding fragments in which one or more antibody domains are truncated or absent (e.g., Fv, Fab, Fab', or F(ab)$_2$ fragments), as well as genetically-engineered antibodies or antigen binding fragments thereof, including single chain antibodies or antibodies that can bind to more than one epitope (e.g., bi-specific antibodies), or antibodies that can bind to one or more different antigens (e.g., bi- or multi-specific antibodies), may also be employed in the invention.

Generally, in the production of an antibody, a suitable experimental animal, such as, for example, but not limited to, a rabbit, a sheep, a hamster, a guinea pig, a mouse, a rat, or a chicken, is exposed to an antigen against which an antibody is desired. Typically, an animal is immunized with an effective amount of antigen that is injected into the animal. An effective amount of antigen refers to an amount needed to induce antibody production by the animal. The animal's immune system is then allowed to respond over a pre-determined period of time. The immunization process can be repeated until the immune system is found to be producing antibodies to the antigen. In order to obtain polyclonal antibodies specific for the antigen, serum is collected from the animal that contains the desired antibodies (or in the case of a chicken, antibody can be collected from the eggs). Such serum is useful as a reagent. Polyclonal antibodies can be further purified from the serum (or eggs) by, for example, treating the serum with ammonium sulfate.

Monoclonal antibodies may be produced according to the methodology of Kohler and Milstein (*Nature* 256:495-497, 1975). For example, B lymphocytes are recovered from the spleen (or any suitable tissue) of an immunized animal and then fused with myeloma cells to obtain a population of hybridoma cells capable of continual growth in suitable culture medium. Hybridomas producing the desired antibody are selected by testing the ability of the antibody produced by the hybridoma to bind to the desired antigen.

The invention also extends to non-antibody polypeptides, sometimes referred to as binding partners, that have been designed to bind specifically to, and either activate or inhibit as appropriate, a protein of the invention. Examples of the design of such polypeptides, which possess a prescribed ligand specificity are given in Beste et al. (*Proc. Natl. Acad. Sci.* 96:1898-1903, 1999), incorporated herein by reference in its entirety.

In yet another embodiment of the invention, the antigen portion of the vaccine is produced as a fusion protein comprising two or more antigens. In one aspect, the fusion protein can include two or more immunogenic domains or two or more epitopes of one or more antigens. In a particularly preferred embodiment, the fusion protein comprises two or more immunogenic domains, and preferably, multiple domains, of an antigen, wherein the multiple domains together encompass several different mutations and/or combinations of mutations that may occur at one or a few positions in the antigen in nature. This provides a particular advantage of being capable of providing a vaccine against a very specific antigen that is known to be variably mutated in a variety of patients. Such a vaccine may provide antigen-specific immunization in a broad range of patients. For example, a multiple domain fusion protein useful in the present invention may have multiple domains, wherein each domain consists of a peptide from a particular protein, the peptide consisting of at least 4 amino acid residues flanking either side of and including a mutated amino acid that is found in the protein, wherein the mutation is associated with a particular disease (e.g., cancer).

Ras is one example of an oncogene in which several mutations are known to occur at particular positions and be associated with the development of one or more types of cancer. Therefore, one can construct fusion proteins that consist of peptides containing a particular residue that is known to be mutated in certain cancers, wherein each domain contains a different mutation at that site in order to cover several or all known mutations at that site. For example, with regard to Ras, one may provide immunogenic domains comprising at least 4 amino acids on either side of and including position 12, wherein each domain has a different substitution for the glycine that normally occurs in the non-mutated Ras protein. In one example, the cancer antigen comprises fragments of at least 5-9 contiguous amino acid residues of a wild-type Ras protein containing amino acid positions 12, 13, 59 or 61 relative to the wild-type Ras protein, wherein the amino acid residues at positions 12, 13, 59 or 61 are mutated with respect to the wild-type Ras protein. In one aspect, the fusion protein construct consists of at least one peptide that is fused in frame with another mutated tumor antigen (e.g., a Ras protein comprising at least one mutation relative to a wild-type Ras protein sequence), wherein the peptide is selected from the group consisting of: (a) a peptide comprising at least from positions 8-16 of SEQ ID NO: 3, wherein the amino acid residue at position 12 with respect to SEQ ID NO:3 is mutated as compared to SEQ ID NO:3; (b) a peptide comprising at least from positions 9-17 of SEQ ID NO:3, wherein the amino acid residue at position 13 with respect to SEQ ID NO:3 is mutated as compared to SEQ ID NO:3; (c) a peptide comprising at least from positions 55-63 of SEQ ID NO:3, wherein the amino acid residue at position 59 with respect to SEQ ID NO:3 is mutated as compared to SEQ ID NO:3; and (d) a peptide comprising at least from positions 57-65 of SEQ ID NO:3, wherein the amino acid residue at position 61 with respect to SEQ ID NO:3 is mutated as compared to SEQ ID NO:3. It is noted that these positions also correspond to any of SEQ ID NOs: 5, 7, 9, 11 or 13, since human and mouse sequences are identical in this region of the protein and since K-Ras, H-Ras and N-Ras are identical in this region.

Other antigens for which such strategies can be particularly useful in the present invention will be apparent to those of skill in the art and include, but are not limited to: any oncogene, TP53 (also known as p53), p73, BRAF, APC, Rb-1, Rb-2, VHL, BRCA1, BRCA2, AR (androgen receptor), Smad4, MDR1, and/or Flt-3.

In one embodiment of the present invention, any of the amino acid sequences described herein can be produced with from at least one, and up to about 20, additional heterologous amino acids flanking each of the C- and/or N-terminal ends of the specified amino acid sequence. The resulting protein or polypeptide can be referred to as "consisting essentially of" the specified amino acid sequence. As discussed above, according to the present invention, the heterologous amino acids are a sequence of amino acids that are not naturally found (i.e., not found in nature, in vivo) flanking the specified amino acid sequence, or that are not related to the function of the specified amino acid sequence, or that would not be encoded by the nucleotides that flank the naturally occurring nucleic acid sequence encoding the specified amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a specified amino acid sequence that can be flanked by from at least one, and up to as many as about 60, additional heterologous nucleotides at each of the 5' and/or the 3' end of the nucleic acid sequence encoding the specified amino acid sequence. The heterologous nucleotides are not naturally found (i.e., not found in nature, in vivo) flanking the nucleic acid sequence encoding the specified amino acid sequence as it occurs in the natural gene or do not encode a protein that imparts any additional function to the protein or changes the function of the protein having the specified amino acid sequence.

Tumor antigens useful in the present invention can include a tumor antigen such as a protein, glycoprotein or surface carbohydrates from a tumor cell, an epitope from a tumor antigen, an entire tumor cell, mixtures of tumor cells, and portions thereof (e.g., lysates). In one embodiment, tumor antigens useful in the present invention can be isolated or derived from an autologous tumor sample. An autologous tumor sample is derived from the animal to whom the therapeutic composition is to be administered. Therefore, such antigens will be present in the cancer against which an immune response is to be elicited. In one aspect, the tumor antigen provided in a vaccine is isolated or derived from at least two, and preferably from a plurality of allogeneic tumor samples of the same histological tumor type. According to the present invention, a plurality of allogeneic tumor samples are tumor samples of the same histological tumor type, isolated from two or more animals of the same species who differ genetically at least within the major histocompatibility complex (MHC), and typically at other genetic loci. Therefore, if administered together, the plurality of tumor antigens can be representative of the substantially all of the tumor antigens present in any of the individuals from which antigen is derived. This embodiment of the method of the present invention provides a vaccine which compensates for natural variations between individual patients in the expression of tumor antigens from tumors of the same histological tumor type.

Therefore, administration of this therapeutic composition is effective to elicit an immune response against a variety of tumor antigens such that the same therapeutic composition can be administered to a variety of different individuals. In some embodiments, antigens from tumors of different histological tumor types can be administered to an animal, in order to provide a very broad vaccine.

Preferably, the tumor from which the antigen is isolated or derived is any tumor or cancer, including, but not limited to, melanomas, squamous cell carcinoma, breast cancers, head and neck carcinomas, thyroid carcinomas, soft tissue sarcomas, bone sarcomas, testicular cancers, prostatic cancers, ovarian cancers, bladder cancers, skin cancers, brain cancers, angiosarcomas, hemangiosarcomas, mast cell tumors, primary hepatic cancers, lung cancers, pancreatic cancers, gastrointestinal cancers, renal cell carcinomas, hematopoietic neoplasias and metastatic cancers thereof. Examples of specific cancer antigens to be used in a vaccine of the present invention include but are not limited to, MAGE (including but not limited to MAGE3, MAGEA6, MAGEA10), NY-ESO-1, gp100, tyrosinase, EGF-R, PSA, PMSA, CEA, HER2/neu, Muc-1, hTERT, MART1, TRP-1, TRP-2, BCR-abl, and mutant oncogenic forms of p53 (TP53), p73, ras, BRAF, APC (adenomatous polyposis coli), myc, VHL (von Hippel's Lindau protein), Rb-1 (retinoblastoma), Rb-2, BRCA1, BRCA2, AR (androgen receptor), Smad4, MDR1, Flt-3.

According to the present invention, a cancer antigen can include any tumor antigen as described above, in addition to any other antigen that is associated with the risk of acquiring or development of cancer or for which an immune response against such antigen can have a therapeutic benefit against a cancer. For example, a cancer antigen could include, but is not limited to, a tumor antigen, a mammalian cell molecule harboring one or more mutated amino acids, a protein normally expressed pre- or neo-natally by mammalian cells, a protein whose expression is induced by insertion of an epidemiologic agent (e.g. virus), a protein whose expression is induced by gene translocation, and a protein whose expression is induced by mutation of regulatory sequences. Some of these antigens may also serve as antigens in other types of diseases (e.g., autoimmune disease).

In one aspect of the invention, the antigen useful in the present composition is an antigen from a pathogen (including the whole pathogen), and particularly, from a pathogen that is associated with (e.g., causes or contributes to) an infectious disease. An antigen from an infectious disease pathogen can include antigens having epitopes that are recognized by T cells, antigens having epitopes that are recognized by B cells, antigens that are exclusively expressed by pathogens, and antigens that are expressed by pathogens and by other cells. Pathogen antigens can include whole cells and the entire pathogen organism, as well as lysates, extracts or other fractions thereof. In some instances, an antigen can include organisms or portions thereof which may not be ordinarily considered to be pathogenic in an animal, but against which immunization is nonetheless desired. The antigens can include one, two or a plurality of antigens that are representative of the substantially all of the antigens present in the infectious disease pathogen against which the vaccine is to be administered. In other embodiments, antigens from two or more different strains of the same pathogen or from different pathogens can be used to increase the therapeutic efficacy and/or efficiency of the vaccine.

According to the present invention, a pathogen antigen includes, but is not limited to, an antigen that is expressed by a bacterium, a virus, a parasite or a fungus. Preferred pathogen antigens for use in the method of the present invention include antigens which cause a chronic infectious disease in an animal. In one embodiment, a pathogen antigen for use in the method or composition of the present invention includes an antigen from a virus. Examples of viral antigens to be used in a vaccine of the present invention include, but are not limited to, env, gag, rev, tar, tat, nucleocapsid proteins and reverse transcriptase from immunodeficiency viruses (e.g., HIV, FIV); HBV surface antigen and core antigen; HCV antigens; influenza nucleocapsid proteins; parainfluenza nucleocapsid proteins; human papilloma type 16 E6 and E7 proteins; Epstein-Barr virus LMP-1, LMP-2 and EBNA-2; herpes LAA and glycoprotein D; as well as similar proteins from other viruses. Particularly preferred antigens for use in the present invention include, but are not limited to, HIV-1 gag, HIV-1 env, HIV-1 pol, HIV-1 tat, HIV-1 nef, HbsAG, HbcAg, hepatitis c core antigen, HPV E6 and E7, HSV glycoprotein D, and *Bacillus anthracis* protective antigen.

Other preferred antigens to include in compositions (vaccines) of the present invention include antigens that are capable of suppressing an undesired, or harmful, immune response, such as is caused, for example, by allergens, autoimmune antigens, inflammatory agents, antigens involved in GVHD, certain cancers, septic shock antigens, and antigens involved in transplantation rejection. Such compounds include, but are not limited to, antihistamines, cyclosporin, corticosteroids, FK506, peptides corresponding to T cell receptors involved in the production of a harmful immune response, Fas ligands (i.e., compounds that bind to the extracellular or the cytosolic domain of cellular Fas receptors, thereby inducing apoptosis), suitable MHC complexes presented in such a way as to effect tolerization or anergy, T cell receptors, and autoimmune antigens, preferably in combination with a biological response modifier capable of enhancing or suppressing cellular and/or humoral immunity.

Other antigens useful in the present invention and combinations of antigens will be apparent to those of skill in the art. The present invention is not restricted to the use of the antigens as described above.

According to the present invention, the term "yeast vehicle-antigen complex" or "yeast-antigen complex" is used generically to describe any association of a yeast vehicle with an antigen. Such association includes expression of the antigen by the yeast (a recombinant yeast), introduction of an antigen into a yeast, physical attachment of the antigen to the yeast, and mixing of the yeast and antigen together, such as in a buffer or other solution or formulation. These types of complexes are described in detail below.

In one embodiment, a yeast cell used to prepare the yeast vehicle is transformed with a heterologous nucleic acid molecule encoding the antigen such that the antigen is expressed by the yeast cell. Such a yeast is also referred to herein as a recombinant yeast or a recombinant yeast vehicle. The yeast cell can then be loaded into the dendritic cell as an intact cell, or the yeast cell can be killed, or it can be derivatized such as by formation of yeast spheroplasts, cytoplasts, ghosts, or subcellular particles, any of which is followed by loading of the derivative into the dendritic cell. Yeast spheroplasts can also be directly transfected with a recombinant nucleic acid molecule (e.g., the spheroplast is produced from a whole yeast, and then transfected) in order to produce a recombinant spheroplast that expresses an antigen.

According to the present invention, an isolated nucleic acid molecule or nucleic acid sequence, is a nucleic acid molecule or sequence that has been removed from its natural milieu. As such, "isolated" does not necessarily reflect the extent to which the nucleic acid molecule has been purified. An isolated nucleic acid molecule useful for transfecting yeast vehicles include DNA, RNA, or derivatives of either DNA or RNA. An isolated nucleic acid molecule can be double stranded or single stranded. An isolated nucleic acid molecule useful in the present invention includes nucleic acid molecules that encode a protein or a fragment thereof, as long as the fragment contains at least one epitope useful in a composition of the present invention.

Nucleic acid molecules transformed into yeast vehicles of the present invention can include nucleic acid sequences encoding one or more proteins, or portions thereof. Such nucleic acid molecules can comprise partial or entire coding regions, regulatory regions, or combinations thereof. One advantage of yeast strains is their ability to carry a number of nucleic acid molecules and of being capable of producing a number of heterologous proteins. A preferred number of antigens to be produced by a yeast vehicle of the present invention is any number of antigens that can be reasonably produced by a yeast vehicle, and typically ranges from at least one to at least about 5 or more, with from about 2 to about 5 compounds being more preferred.

A peptide or protein encoded by a nucleic acid molecule within a yeast vehicle can be a full-length protein, or can be a functionally equivalent protein in which amino acids have been deleted (e.g., a truncated version of the protein), inserted, inverted, substituted and/or derivatized (e.g., acetylated, glycosylated, phosphorylated, tethered by a glycerophosphatidyl inositol (GPI) anchor) such that the modified protein has a biological function substantially similar to that of the natural protein (or which has enhanced or inhibited function as compared to the natural protein, if desired). Modifications can be accomplished by techniques known in the art including, but not limited to, direct modifications to the protein or modifications to the nucleic acid sequence encoding the protein using, for example, classic or recombinant DNA techniques to effect random or targeted mutagenesis. Functionally equivalent proteins can be selected using assays that measure the biological activity of the protein.

Expression of an antigen in a yeast vehicle of the present invention is accomplished using techniques known to those skilled in the art. Briefly, a nucleic acid molecule encoding at least one desired antigen is inserted into an expression vector in such a manner that the nucleic acid molecule is operatively linked to a transcription control sequence in order to be capable of effecting either constitutive or regulated expression of the nucleic acid molecule when transformed into a host yeast cell. Nucleic acid molecules encoding one or more antigens can be on one or more expression vectors operatively linked to one or more transcription control sequences.

In a recombinant molecule of the present invention, nucleic acid molecules are operatively linked to expression vectors containing regulatory sequences such as transcription control sequences, translation control sequences, origins of replication, and other regulatory sequences that are compatible with the yeast cell and that control the expression of nucleic acid molecules. In particular, recombinant molecules of the present invention include nucleic acid molecules that are operatively linked to one or more transcription control sequences. The phrase "operatively linked" refers to linking a nucleic acid molecule to a transcription control sequence in a manner such that the molecule is able to be expressed when transfected (i.e., transformed, transduced or transfected) into a host cell.

Transcription control sequences, which can control the amount of protein produced, include sequences which control the initiation, elongation, and termination of transcription. Particularly important transcription control sequences are those which control transcription initiation, such as promoter and upstream activation sequences. Any suitable yeast promoter can be used in the present invention and a variety of such promoters are known to those skilled in the art. Preferred promoters for expression in *Saccharomyces cerevisiae* include, but are not limited to, promoters of genes encoding the following yeast proteins: alcohol dehydrogenase I (ADH1) or II (ADH2), CUP1, phosphoglycerate kinase (PGK), triose phosphate isomerase (TPI), glyceraldehyde-3-phosphate dehydrogenase (GAPDH; also referred to as TDH3, for triose phosphate dehydrogenase), galactokinase (GAL1), galactose-1-phosphate uridyl-transferase (GAL7), UDP-galactose epimerase (GAL10), cytochrome $c_1$ (CYC1), Sec7 protein (SEC7) and acid phosphatase (PHO5), with hybrid promoters such as ADH2/GAPDH and CYC1/GAL10 promoters being more preferred, and the ADH2/GAPDH promoter, which is induced when glucose concentrations in the cell are low (e.g., about 0.1 to about 0.2 percent), being even more preferred. Likewise, a number of upstream activation sequences (UASs), also referred to as enhancers, are known. Preferred upstream activation sequences for expression in *Saccharomyces cerevisiae* include, but are not limited to, the UASs of genes encoding the following proteins: PCK1, TPI, TDH3,CYC1, ADH1, ADH2, SUC2, GAL1, GAL7 and GAL10, as well as other UASs activated by the GAL4 gene product, with the ADH2 UAS being particularly preferred. Since the ADH2 UAS is activated by the ADR1 gene product, it is preferable to overexpress the ADR1 gene when a heterologous gene is operatively linked to the ADH2 UAS. Preferred transcription termination sequences for expression in *Saccharomyces cerevisiae* include the termination sequences of the α-factor, GAPDH, and CYC1 genes.

Preferred transcription control sequences to express genes in methyltrophic yeast include the transcription control regions of the genes encoding alcohol oxidase and formate dehydrogenase.

Transfection of a nucleic acid molecule into a yeast cell according to the present invention can be accomplished by any method by which a nucleic acid molecule administered into the cell and includes, but is not limited to, diffusion, active transport, bath sonication, electroporation, microinjection, lipofection, adsorption, and protoplast fusion. Transfected nucleic acid molecules can be integrated into a yeast chromosome or maintained on extrachromosomal vectors using techniques known to those skilled in the art. Examples of yeast vehicles carrying such nucleic acid molecules are disclosed in detail herein. As discussed above, yeast cytoplast, yeast ghost, and subcellular yeast membrane extract or fractions thereof can also be produced recombinantly by transfecting intact yeast microorganisms or yeast spheroplasts with desired nucleic acid molecules, producing the antigen therein, and then further manipulating the microorganisms or spheroplasts using techniques known to those skilled in the art to produce cytoplast, ghost or subcellular yeast membrane extract or fractions thereof containing desired antigens.

Effective conditions for the production of recombinant yeast vehicles and expression of the antigen by the yeast vehicle include an effective medium in which a yeast strain can be cultured. An effective medium is typically an aqueous medium comprising assimilable carbohydrate, nitrogen and phosphate sources, as well as appropriate salts, minerals, metals and other nutrients, such as vitamins and growth factors. The medium may comprise complex nutrients or may be a defined minimal medium. Yeast strains of the present invention can be cultured in a variety of containers, including, but not limited to, bioreactors, erlenmeyer flasks, test tubes, microtiter dishes, and petri plates. Culturing is carried out at a temperature, pH and oxygen content appropriate for the yeast strain. Such culturing conditions are well within the expertise of one of ordinary skill in the art (see, for example, Guthrie et al. (eds.), 1991, *Methods in Enzymology*, vol. 194, Academic Press, San Diego).

In one embodiment of the present invention, as an alternative to expression of an antigen recombinantly in the yeast vehicle, a yeast vehicle is loaded intracellularly with the protein or peptide antigen, or with carbohydrates or other molecules that serve as an antigen. Subsequently, the yeast vehicle, which now contains the antigen intracellularly, can be administered to the patient or loaded into a carrier such as a dendritic cell (described below). As used herein, a peptide comprises an amino acid sequence of less than or equal to about 30-50 amino acids, while a protein comprises an amino acid sequence of more than about 30-50 amino acids; proteins can be multimeric. A protein or peptide useful as an antigen can be as small as a T cell epitope (i.e., greater than 5 amino acids in length) and any suitable size greater than that which comprises multiple epitopes, protein fragments, full-length proteins, chimeric proteins or fusion proteins. Peptides and proteins can be derivatized either naturally or synthetically; such modifications can include, but are not limited to, glycosylation, phosphorylation, acetylation, myristylation, prenylation, palmitoylation, amidation and/or addition of glycerophosphatidyl inositol. Peptides and proteins can be inserted directly into yeast vehicles of the present invention by techniques known to those skilled in the art, such as by diffusion, active transport, liposome fusion, electroporation, phagocytosis, freeze-thaw cycles and bath sonication. Yeast vehicles that can be directly loaded with peptides, proteins, carbohydrates, or other molecules include intact yeast, as well as spheroplasts, ghosts or cytoplasts, which can be loaded with antigens after production, but before loading into dendritic cells. Alternatively, intact yeast can be loaded with the antigen, and then spheroplasts, ghosts, cytoplasts, or subcellular particles can be prepared therefrom. Any number of antigens can be loaded into a yeast vehicle in this embodiment, from at least 1, 2, 3, 4 or any whole integer up to hundreds or thousands of antigens, such as would be provided by the loading of a microorganism, by the loading of a mammalian tumor cell, or portions thereof, for example.

In another embodiment of the present invention, an antigen is physically attached to the yeast vehicle. Physical attachment of the antigen to the yeast vehicle can be accomplished by any method suitable in the art, including covalent and non-covalent association methods which include, but are not limited to, chemically crosslinking the antigen to the outer surface of the yeast vehicle or biologically linking the antigen to the outer surface of the yeast vehicle, such as by using an antibody or other binding partner. Chemical cross-linking can be achieved, for example, by methods including glutaraldehyde linkage, photoaffinity labeling, treatment with carbodiimides, treatment with chemicals capable of linking di-sulfide bonds, and treatment with other cross-linking chemicals standard in the art. Alternatively, a chemical can be contacted with the yeast vehicle that alters the charge of the lipid bilayer of yeast membrane or the composition of the cell wall so that the outer surface of the yeast is more likely to fuse or bind to antigens having particular charge characteristics. Targeting agents such as antibodies, binding peptides, soluble receptors, and other ligands may also be incorporated into an antigen as a fusion protein or otherwise associated with an antigen for binding of the antigen to the yeast vehicle.

In yet another embodiment, the yeast vehicle and the antigen are associated with each other by a more passive, non-specific or non-covalent binding mechanism, such as by gently mixing the yeast vehicle and the antigen together in a buffer or other suitable formulation. In one embodiment of the invention, the yeast vehicle and the antigen are both loaded intracellularly into a carrier such as a dendritic cell or macrophage to form the therapeutic composition or vaccine of the present invention. Various forms in which the loading of both components can be accomplished are discussed in detail below. As used herein, the term "loaded" and derivatives thereof refer to the insertion, introduction, or entry of a component (e.g., the yeast vehicle and/or antigen) into a cell (e.g., a dendritic cell). To load a component intracellularly refers to the insertion or introduction of the component to an intracellular compartment of the cell (e.g., through the plasma membrane and at a minimum, into the cytoplasm, a phagosome, a lysosome, or some intracellular space of the cell). To load a component into a cell references any technique by which the component is either forced to enter the cell (e.g., by electroporation) or is placed in an environment (e.g., in contact with or near to a cell) where the component will be substantially likely to enter the cell by some process (e.g., phagocytosis). Loading techniques include, but are not limited to: diffusion, active transport, liposome fusion, electroporation, phagocytosis, and bath sonication. In a preferred embodiment, passive mechanisms for loading a dendritic cell with the yeast vehicle and/or antigen are used, such passive mechanisms including phagocytosis of the yeast vehicle and/or antigen by the dendritic cell.

In one embodiment of the present invention, a composition of vaccine can also include biological response modifier compounds, or the ability to produce such modifiers (i.e., by transfection with nucleic acid molecules encoding such modifiers), although such modifiers are not necessary to achieve a robust immune response according to the invention. For example, a yeast vehicle can be transfected with or loaded with at least one antigen and at least one biological response modifier compound. Biological response modifiers are compounds that can modulate immune responses. Certain biological response modifiers can stimulate a protective immune response whereas others can suppress a harmful immune response. Certain biological response modifiers preferentially enhance a cell-mediated immune response whereas others preferentially enhance a humoral immune response (i.e., can stimulate an immune response in which there is an increased level of cellular compared to humoral immunity, or vice versa.). There are a number of techniques known to those skilled in the art to measure stimulation or suppression of immune responses, as well as to differentiate cellular immune responses from humoral immune responses.

Suitable biological response modifiers include cytokines, hormones, lipidic derivatives, small molecule drugs and other growth modulators, such as, but not limited to, interleukin 2 (IL-2), interleukin 4 (IL-4), interleukin 10 (IL-10), interleukin 12 (IL-12), interferon gamma (IFN-gamma) insulin-like growth factor I (IGF-I), transforming growth factor beta (TGF-β) steroids, prostaglandins and leukotrienes. The ability of a yeast vehicle to express (i.e., produce), and possibly secrete, IL-2, IL-12 and/or IFN-gamma preferentially enhances cell-mediated immunity, whereas the ability of a yeast vehicle to express, and possibly secrete, IL-4, IL-5 and/or IL-10 preferentially enhances humoral immunity.

Yeast vehicles of the present invention can be associated with a wide variety of antigens capable of protecting an animal from disease, and this ability can be further enhanced by loading the yeast vehicle and antigen into a dendritic cell or macrophage to form a vaccine of the present invention. Accordingly, the method of use of the therapeutic composition or vaccine of the present invention preferably elicits an immune response in an animal such that the animal is protected from a disease that is amenable to elicitation of an immune response, including cancer or an infectious disease. As used herein, the phrase "protected from a disease" refers to reducing the symptoms of the disease; reducing the occurrence of the disease, and/or reducing the severity of the disease. Protecting an animal can refer to the ability of a therapeutic composition of the present invention, when administered to an animal, to prevent a disease from occurring and/or to cure or to alleviate disease symptoms, signs or causes. As such, to protect an animal from a disease includes both preventing disease occurrence (prophylactic treatment or prophylactic vaccine) and treating an animal that has a disease or that is experiencing initial symptoms of a disease (therapeutic treatment or a therapeutic vaccine). In particular, protecting an animal from a disease is accomplished by eliciting an immune response in the animal by inducing a beneficial or protective immune response which may, in some instances, additionally suppress (e.g., reduce, inhibit or block) an overactive or harmful immune response. The term, "disease" refers to any deviation from the normal health of an animal and includes a state when disease symptoms are present, as well as conditions in which a deviation (e.g., infection, gene mutation, genetic defect, etc.) has occurred, but symptoms are not yet manifested.

More specifically, a vaccine as described herein, when administered to an animal by the method of the present invention, preferably produces a result which can include alleviation of the disease (e.g., reduction of at least one symptom or clinical manifestation of the disease), elimination of the disease, reduction of a tumor or lesion associated with the disease, elimination of a tumor or lesion associated with the disease, prevention or alleviation of a secondary disease resulting from the occurrence of a primary disease (e.g., metastatic cancer resulting from a primary cancer), prevention of the disease, and stimulation of effector cell immunity against the disease.

Cancers to be treated or prevented using the method and composition of the present invention include, but are not limited to, melanomas, squamous cell carcinoma, breast cancers, head and neck carcinomas, thyroid carcinomas, soft tissue sarcomas, bone sarcomas, testicular cancers, prostatic cancers, ovarian cancers, bladder cancers, skin cancers, brain cancers, angiosarcomas, hemangiosarcomas, mast cell tumors, primary hepatic cancers, lung cancers, pancreatic cancers, gastrointestinal cancers, renal cell carcinomas, hematopoietic neoplasias, and metastatic cancers thereof. Particularly preferred cancers to treat with a therapeutic composition of the present invention include primary lung cancers, pulmonary metastatic cancers, primary brain cancers, and metastatic brain cancers. A preferred brain cancer to treat includes, but is not limited to, glioblastoma multiforme. Preferred lung cancers to treat include, but are not limited to, non-small cell carcinomas, small cell carcinomas and adenocarcinomas. A therapeutic composition of the present invention is useful for eliciting an immune response in an animal to treat tumors that can form in such cancers, including malignant and benign tumors. Preferably, expression of the tumor antigen in a tissue of an animal that has cancer produces a result selected from the group of alleviation of the cancer, reduction of a tumor associated with the cancer, elimination of a tumor associated with the cancer, prevention of metastatic cancer, prevention of the cancer and stimulation of effector cell immunity against the cancer.

One particular advantage of the present invention is that the therapeutic composition does not need to be administrated with an immunopotentiator such as an adjuvant or a carrier, since the yeast vehicle and antigen combination elicits a potent immune response in the absence of additional adjuvants, which is again enhanced by loading of these components into a dendritic cell, as described in U.S. application Ser. No. 09/991,363, supra. This characteristic, however, does not preclude the use of immunopotentiators in compositions of the present invention. As such, in one embodiment, a composition of the present invention can include one or more adjuvants and/or carriers.

Adjuvants are typically substances that generally enhance the immune response of an animal to a specific antigen. Suitable adjuvants include, but are not limited to, Freund's adjuvant; other bacterial cell wall components; aluminum-based salts; calcium-based salts; silica; polynucleotides; toxoids; serum proteins; viral coat proteins; other bacterial-derived preparations; gamma interferon; block copolymer adjuvants, such as Hunter's Titermax adjuvant (CytRx™, Inc. Norcross, Ga.); Ribi adjuvants (available from Ribi ImmunoChem Research, Inc., Hamilton, Mont.); and saponins and their derivatives, such as Quil A (available from Superfos Biosector A/S, Denmark).

Carriers are typically compounds that increase the half-life of a therapeutic composition in the treated animal. Suitable carriers include, but are not limited to, polymeric controlled release formulations, biodegradable implants, liposomes, oils, esters, and glycols.

Therapeutic compositions of the present invention can also contain one or more pharmaceutically acceptable excipients. As used herein, a pharmaceutically acceptable excipient refers to any substance suitable for delivering a therapeutic composition useful in the method of the present invention to a suitable in vivo or ex vivo site. Preferred pharmaceutically acceptable excipients are capable of maintaining a yeast vehicle (or a dendritic cell comprising the yeast vehicle) in a form that, upon arrival of the yeast vehicle or cell at a target cell, tissue, or site in the body, the yeast vehicle (associated with an antigen) or the dendritic cell (loaded with a yeast vehicle and antigen), is capable of eliciting an immune response at the target site (noting that the target site can be systemic). Suitable excipients of the present invention include excipients or formularies that transport, but do not specifically target the vaccine to a site (also referred to herein as non-targeting carriers). Examples of pharmaceutically acceptable excipients include, but are not limited to, water, saline, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- or o-cresol, formalin and benzol alcohol.

The present invention includes the delivery of a composition or vaccine of the invention to an animal. The administration process can be performed ex vivo or in vivo. Ex vivo administration refers to performing part of the regulatory step outside of the patient, such as administering a composition of the present invention to a population of cells (dendritic cells) removed from a patient under conditions such that the yeast vehicle and antigen are loaded into the cell, and returning the cells to the patient. The therapeutic composition of the present invention can be returned to a patient, or administered to a patient, by any suitable mode of administration.

Administration of a vaccine or composition, including a dendritic cell loaded with the yeast vehicle and antigen, can be systemic, mucosal and/or proximal to the location of the target site (e.g., near a tumor). The preferred routes of administration will be apparent to those of skill in the art, depending on the type of condition to be prevented or treated, the antigen used, and/or the target cell population or tissue. Preferred methods of administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, subcutaneous administration, intraarticular administration, intraventricular administration, inhalation (e.g., aerosol), intracranial, intraspinal, intraocular, aural, intranasal, oral, pulmonary administration, impregnation of a catheter, and direct injection into a tissue. Particularly preferred routes of administration include: intravenous, intraperitoneal, subcutaneous, intradermal, intranodal, intramuscular, transdermal, inhaled, intranasal, oral, intraocular, intraarticular, intracranial, and intraspinal. Parenteral delivery can include intradermal, intramuscular, intraperitoneal, intrapleural, intrapulmonary, intravenous, subcutaneous, atrial catheter and venal catheter routes. Aural delivery can include ear drops, intranasal delivery can include nose drops or intranasal injection, and intraocular delivery can include eye drops. Aerosol (inhalation) delivery can also be performed using methods standard in the art (see, for example, Stribling et al., *Proc. Natl. Acad. Sci. USA* 189:11277-11281, 1992, which is incorporated herein by reference in its entirety). For example, in one embodiment, a composition or vaccine of the invention can be formulated into a composition suitable for nebulized delivery using a suitable inhalation device or nebulizer. Oral delivery can include solids and liquids that can be taken through the mouth, and is useful in the development of mucosal immunity and since compositions comprising yeast vehicles can be easily prepared for oral delivery, for example, as tablets or capsules, as well as being formulated into food and beverage products. Other routes of administration that modulate mucosal immunity are useful in the treatment of viral infections, epithelial cancers, immunosuppressive disorders and other diseases affecting the epithelial region. Such routes include bronchial, intradermal, intramuscular, intranasal, other inhalatory, rectal, subcutaneous, topical, transdermal, vaginal and urethral routes.

A more preferred route of delivery is any route of delivery of a composition or vaccine to the respiratory system, including, but not limited to, inhalation, intranasal, intratracheal, and the like. As discussed above and shown in the Examples, the present inventors have shown that administration of a vaccine of the invention by this route of administration provides enhanced results as compared to at least subcutaneous delivery, and appears to be particularly efficacious for the treatment of brain cancers and lung cancers.

According to the present invention, an effective administration protocol (i.e., administering a vaccine or therapeutic composition in an effective manner) comprises suitable dose parameters and modes of administration that result in elicitation of an immune response in an animal that has a disease or condition, or that is at risk of contracting a disease or condition, preferably so that the animal is protected from the disease. Effective dose parameters can be determined using methods standard in the art for a particular disease. Such methods include, for example, determination of survival rates, side effects (i.e., toxicity) and progression or regression of disease. In particular, the effectiveness of dose parameters of a therapeutic composition of the present invention when treating cancer can be determined by assessing response rates. Such response rates refer to the percentage of treated patients in a population of patients that respond with either partial or complete remission. Remission can be determined by, for example, measuring tumor size or microscopic examination for the presence of cancer cells in a tissue sample.

In accordance with the present invention, a suitable single dose size is a dose that is capable of eliciting an antigen-specific immune response in an animal when administered one or more times over a suitable time period. Doses can vary depending upon the disease or condition being treated. In the treatment of cancer, for example, a suitable single dose can be dependent upon whether the cancer being treated is a primary tumor or a metastatic form of cancer. One of skill in the art can readily determine appropriate single dose sizes for administration based on the size of an animal and the route of administration.

A suitable single dose of a therapeutic composition or vaccine of the present invention is a dose that is capable of effectively providing a yeast vehicle and an antigen to a given cell type, tissue, or region of the patient body in an amount effective to elicit an antigen-specific immune response, when administered one or more times over a suitable time period. For example, in one embodiment, a single dose of a yeast vehicle of the present invention is from about $1\times10^5$ to about $5\times10^7$ yeast cell equivalents per kilogram body weight of the organism being administered the composition. More preferably, a single dose of a yeast vehicle of the present invention is from about 0.1 Y.U. ($1\times10^6$ cells) to about 100 Y.U. ($1\times10^9$ cells) per dose (i.e., per organism), including any interim dose, in increments of $0.1\times10^6$ cells (i.e., $1.1\times10^6$, $1.2\times10^6$, $1.3\times10^6$ ...). This range of doses can be effectively used in any organism of any size, including mice, monkeys, humans, etc. When the vaccine is administered by loading the yeast vehicle and antigen into dendritic cells, a preferred single dose of a vaccine of the present invention is from about $0.5\times10^6$ to about $40\times10^6$ dendritic cells per individual per administration. Preferably, a single dose is from about $1\times10^6$ to about $20\times10^6$ dendritic cells per individual, and more preferably from about $1\times10^6$ to about $10\times10^6$ dendritic cells per individual. "Boosters" of a therapeutic composition are preferably administered when the immune response against the antigen has waned or as needed to provide an immune response or induce a memory response against a particular antigen or antigen(s). Boosters can be administered from about 2 weeks to several years after the original administration. In one embodiment, an administration schedule is one in which from about $1\times10^5$ to about $5\times10^7$ yeast cell equivalents of a composition per kg body weight of the organism is administered from about one to about 4 times over a time period of from about 1 month to about 6 months.

It will be obvious to one of skill in the art that the number of doses administered to an animal is dependent upon the extent of the disease and the response of an individual patient to the treatment. For example, a large tumor may require more doses than a smaller tumor, and a chronic disease may require more doses than an acute disease. In some cases, however, a patient having a large tumor may require fewer doses than a patient with a smaller tumor, if the patient with the large tumor responds more favorably to the therapeutic composition than the patient with the smaller tumor. Thus, it is within the scope of the present invention that a suitable number of doses includes any number required to treat a given disease.

In another aspect of the invention, the method of treatment of a disease or condition such as cancer can be combined with other therapeutic approaches to enhance the efficacy of the treatment. For example, in the treatment of cancer, the administration of the vaccine of the present invention can occur after surgical resection of a tumor from the animal. In another aspect, administration of the vaccine occurs after surgical resection of a tumor from the animal and after administration of non-myeloablative allogeneic stem cell transplantation (discussed below). In yet another aspect, administration of the vaccine occurs after surgical resection of a tumor from the animal, after administration of non-myeloablative allogeneic stem cell transplantation, and after allogeneic donor lymphocyte infusion.

Another embodiment of the present invention relates to a method to treat a patient that has cancer, comprising: (a) treating a patient that has cancer by nonmyeloablative stem cell transfer effective to establish a stable mixed bone marrow chimerism, wherein the stem cells are provided by an allogeneic donor; (b) administering lymphocytes obtained from the allogeneic donor to the patient; and (c) administering to the patient, after step (b), a vaccine comprising a yeast vehicle and at least one cancer antigen. The process of establishing a stable mixed bone marrow chimerism via non-myeloablative allogeneic stem cell transplantation has been previously described in detail in Luznik et al. (*Blood* 101(4): 1645-1652, 2003) and elsewhere in the art (e.g., Appelbaum et al., 2001, *Hematology* pp. 62-86). Briefly, a patient is treated with non-lethal, non-myeloablative total body irradiation and immunosuppression (e.g., combination radiation and chemotherapy) and is administered a population of cells containing stem cells (e.g., bone marrow) from an allogeneic donor. This treatment will result in the establishment of stable, mixed bone marrow chimerism in the recipient patient (i.e., both donor and host immune cells exist). In the protocol of Luznik et al., the recipient is then provided with an infusion of donor lymphocytes, followed by a vaccine of autologous tumor cells, a source of GM-CSF and a source of histocompatibility antigens. This treatment resulted in long term tumor free survival of a significant number of the experimental animals.

The present invention provides an improvement to the non-myeloablative allogeneic stem cell transplantation and tumor cell vaccination protocol by combining the non-myeloablative allogeneic stem cell transplantation with a yeast-based vaccine strategy of the present invention. As exemplified in Example 5, the method of the present invention is as effective at treating tumors as the protocol of Luznik et al., but does not require the use of autologous tumor antigens from the recipient, nor the use of biological response modifiers or other adjuvants (e.g., the GM-CSF and source of histocompatibility antigens) as provided in the prior protocol. The modified method of the present invention provides additional advantages of enabling the use of a wide variety of very specific antigen selections and combinations in the vaccine, and of providing a vaccine for a broad spectrum of cancer patients, whereas the prior protocol, by utilizing autologous tumor cells from the recipient, is effectively limited to that patient. The present invention also provides for the vaccination of the donor of stem cells and lymphocytes with the yeast-based vaccine of the invention, which can express the same or slightly different antigens as the vaccine to be administered to the recipient, which is expected to further enhance the efficacy of the vaccine.

In this embodiment of the invention, the step of treating a patient that has cancer by nonmyeloablative stem cell transfer effective to establish a stable mixed bone marrow chimerism, wherein the stem cells are provided by an allogeneic donor is performed as has been well described in the art (e.g., Luznik et al., supra; Appelbaum et al., 2001, *Hematology* pp. 62-86). The allogeneic lymphocyte infusion of step (b) can be performed by any suitable method, including collection of allogeneic lymphocytes from peripheral blood of the donor and infusion into the recipient patient, such as by Ultrapheresis techniques known in the art. Finally, the patient is administered the yeast-based vaccine of the invention as previously described herein. In one aspect of this embodiment, the method further includes administering to the donor, prior to step (a), a vaccine comprising a yeast vehicle and at least one cancer antigen. In another aspect, the method includes removing a tumor from the patient prior to performing step (a).

In the method of the present invention, vaccines and therapeutic compositions can be administered to any member of the Vertebrate class, Mammalia, including, without limitation, primates, rodents, livestock and domestic pets. Livestock include mammals to be consumed or that produce useful products (e.g., sheep for wool production). Preferred mammals to protect include humans, dogs, cats, mice, rats, goats, sheep, cattle, horses and pigs, with humans being particularly preferred. According to the present invention, the term "patient" can be used to describe any animal that is the subject of a diagnostic, prophylactic, or therapeutic treatment as described herein.

The following experimental results are provided for purposes of illustration and are not intended to limit the scope of the invention.

EXAMPLES

Example 1

The following example demonstrates the administration of a yeast based vaccine comprising a cancer antigen for the treatment of a non-small cell lung carcinoma (NSCLC) in vivo.

Ras mutations are common in pulmonary adenocarcinomas of humans, mice, rats and hamsters. In fact, mutations in the ras proto-oncogene family are the most common oncogene-related mutations in human cancer and in tumors in experimental animals. The present inventors tested whether yeast-based vaccines which have now been designed to be directed to mutant protein-specific ras mutations, can induce productive immune responses that lead to tumor destruction in mouse lung adenocarcinoma models. The overall goal of the experiments was to establish that such a vaccine could be used to combat lung cancer in humans.

The model used in the experiments described herein is a mouse model in which A/J mice are injected with urethane (ethyl carbamate, which is metabolized to vinyl carbamate, the presumptive carcinogenic metabolite). Hyperplasias are seen in about 6 weeks, benign tumors at 8-10 weeks with the first signs of malignancy after 8 months. By 10 months the tumors can occupy the whole lung lobe and at 12 months the mice die from respiratory distress. In this experiment, a single K-ras mutation is expressed in the tumor cells, which is in the codon encoding the amino acid residue at position 61 (also referred to as codon 61).

The present inventors have produced Ras61-VAX (GlobeImmune), which is a strain of yeast that has been engineered to expresses mouse K-ras protein with a mutation at codon 61 (relative to the K-ras sequence of SEQ ID NO:5), which is the mutant K-ras protein expressed in spontaneously induced mouse lung tumors and mouse lung tumor cell lines. Animals immunized with the Ras61-VAX directed against codon 61 mutations were tested for their ability to prevent the development of tumors or reduce their size after induction in the urethane induction model.

The results demonstrated that animals immunized with Ras61-VAX show significant protection against pre-existing lung tumors spontaneously induced by urethane exposure in mice. Both the number of tumors and the size of tumors was significantly reduced in vaccinated animals, compared to control animals (FIG. 1). These results demonstrate the feasibility and utility of therapeutic intervention using the present inventors' yeast-based vaccines that express mutant K-ras proteins to treat and/or prevent disease caused by a cancer.

Figure 2:
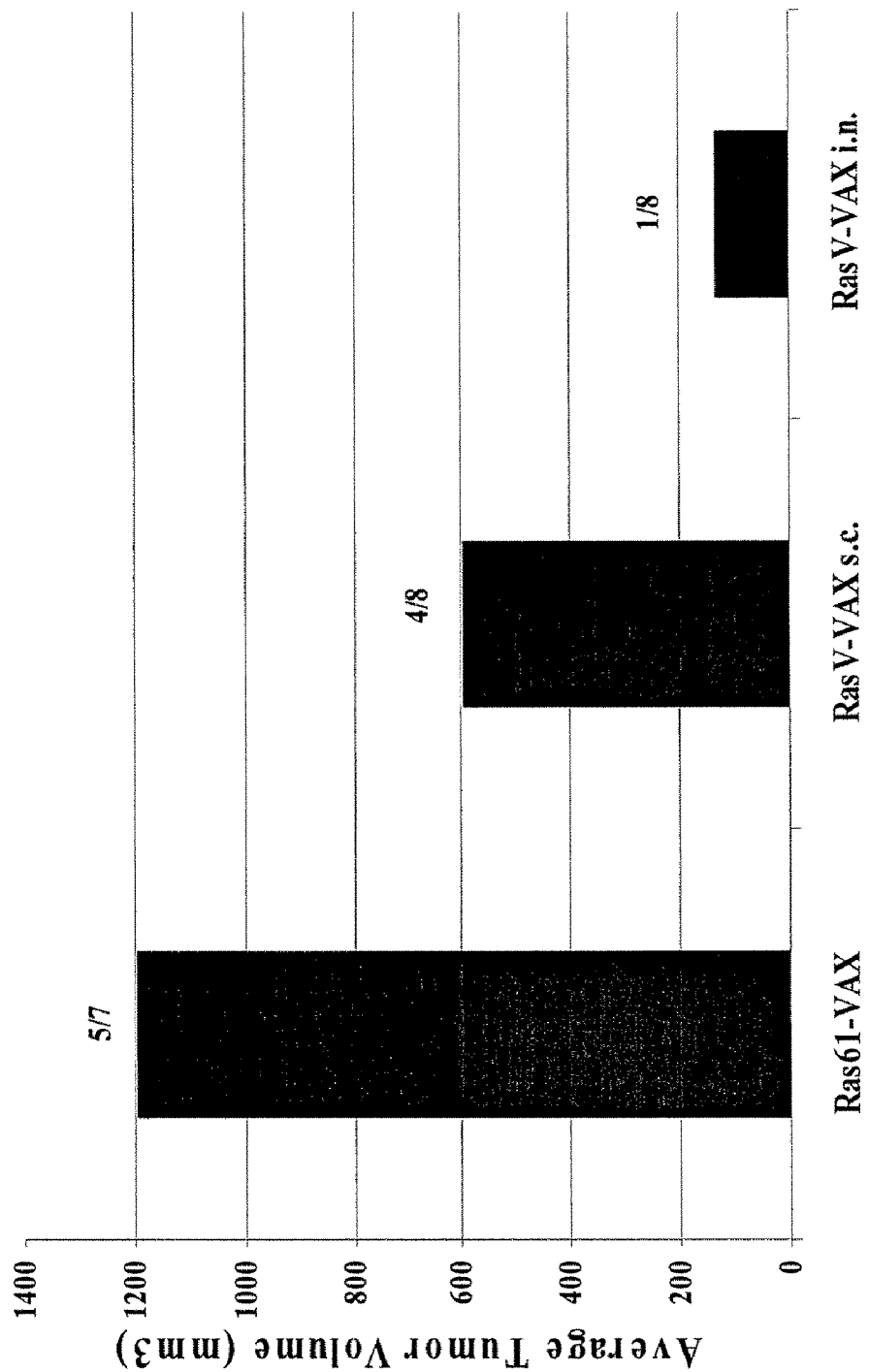
FIG. 2 is a bar graph showing that yeast-based RasV-VAX vaccine provides specific protection against lung tumor growth when administered by subcutaneous and intranasal routes.

In addition, FIG. 2 shows the results of an experiment in which C57BL/6 mice were immunized by subcutaneous administration of Ras61-VAX (Q61R alone) or by intranasal versus subcutaneous administration of a yeast vaccine expressing a mutant Ras having two mutations (RasV-VAX; G12V+Q61R), on days 1, 8, 22 and 36. Mice were challenged with 10,000 CMT64 cells by subcutaneous administration on day 29, where CMT64 cells endogenously express a mutant K-ras protein altered at amino acid 12 from glycine to valine (G12V). FIG. 2 shows the size of tumors on day 59 (30 days after challenge) and the number of animals with tumors/total number of animals (above bar). As shown in FIG. 2, administration of the Ras61-VAX again provided minimal protection against lung tumor growth (2 out of 7 animals are tumor-free), and administration of RasV-Vax provided specific immunotherapeutic protection by significantly reducing tumor volume and numbers (4 out of 8 animals vaccinated subcutaneously are tumor-free and 7 out of 8 animals vaccinated intranasally are tumor-free). Surprisingly, intranasal administration of the vaccine provided superior results as compared to the subcutaneous administration of the same vaccine. These results highlighted the specificity of molecular immunotherapy with the yeast-based vaccine products. These studies revealed the requirement that immune-mediated rejection of tumor growth was dependent on the administration of yeast-based vaccines with the tumor antigen harboring the relevant mutated amino acid.

Example 2

The following example demonstrates the use of a yeast-based vaccine comprising a cancer antigen to treat a brain tumor in vivo.

Figure 3:
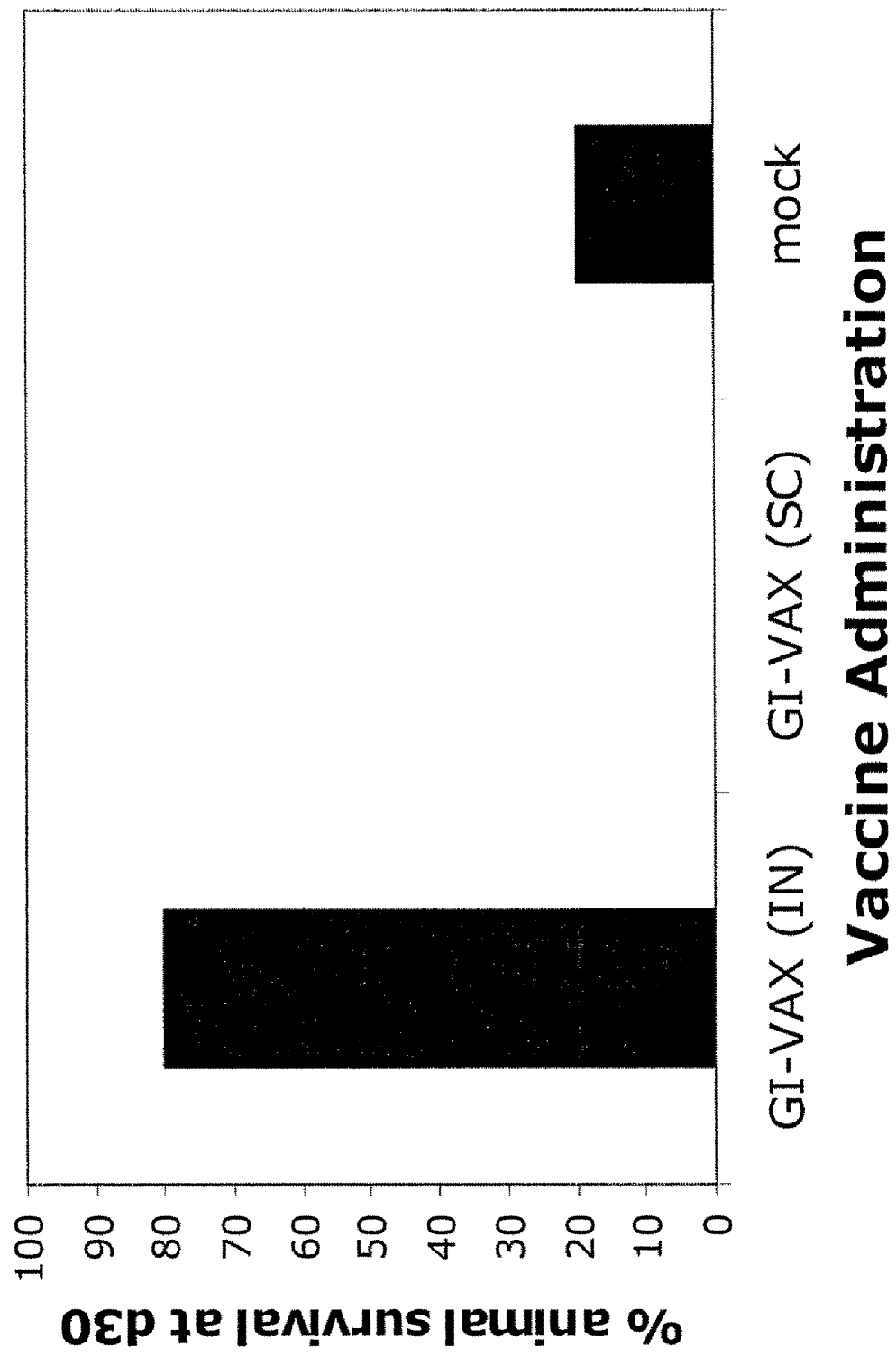
FIG. 3 is bar graph showing that a Gag-expressing yeast based vaccine protects against intracranial tumors when the vaccine is administered by intranasal, but not subcutaneous, administration.

In the following experiment, groups of 5 mice were immunized twice (day 0 and day 7) with Gag protein-expressing vaccine (GI-VAX) or PBS (mock injected) by subcutaneous injection or intranasal administration, then challenged on day 14 with tumors expressing the Gag protein. The results from two independent studies revealed prolonged survival against intracranial tumor challenge in mice receiving the vaccine by intranasal administration, as compared to mock-injected mice, and surprisingly, as compared to animals receiving the vaccine by a subcutaneous route (FIG. 3). Subcutaneous immunization did protect animals against subcutaneous tumor challenge (data not shown). These results show that the method of the present invention can be used effectively when administered intranasally and that administration to the respiratory tract may be efficacious for intracranial tumors where other routes of administration are not.

Example 3

The following example demonstrates the use of a yeast-based vaccine comprising a human cancer antigen (epidermal growth factor receptor; EGFR) to treat a melanoma and a brain tumor in vivo.

The ability of immunotherapeutic strategies to elicit protective immune responses is dependent on a number of important variables. First, the vaccine must be able to activate the immune system to recognize the target antigen, i.e. to provide "adjuvant" activity. In the case of the yeast-based vaccine, the inventors had previously shown that uptake of yeast into dendritic cells upregulated MHC class I and class II protein expression, and to trigger cytokine production, which are the hallmarks of adjuvant activity (Stubbs et al, Nature Med (2001) 7, 625-629). The degree to which yeast activate the 'innate' immune system was equivalent to that seen by using lipopolysaccharide (LPS) derived from bacterial cell walls. Second, the vaccine must promote surface presentation of the immunodominant epitopes of the target antigens to the immune system. The inventors had previously demonstrated that the yeast-based vaccine is very potent for delivering antigenic epitopes for stimulation of the cell-mediated (CTL) and the humoral (antibody) responses of the immune system (Stubbs et al, Nature Medicine (2001) 7, 625-629). Third, and most importantly, stimulation of the immune system must trigger immune responses to sites in the body where they are needed. As shown below, surprisingly, the route of vaccine administration appears to influence the efficacy of the immune response against tumors that develop in different sites in the body.

To test the immunogenicity of an EGFR-tm VAX (a yeast vaccine of the invention expressing EGFR as the cancer antigen), it was necessary to modify the glioma tumor cells used in the challenge experiments. B16 mouse melanoma cells and 9L rat glioma tumor cells were transfected to express human EGFR (B16-E cells and 9L-E cells, respectively). The cloned 9L-E cell line was subsequently sorted for cells that express high, intermediate or low levels of hEGFR. The B16-E cells and the 9L-E cells therefore possess the antigen included in the yeast vaccine (i.e. human EGFR), and provide an appropriate surrogate model for human gliomas that exhibit altered expression of EGFR in the malignant cells. The goal of the studies was to demonstrate that the yeast-based delivery vehicle triggered protective immunity against challenge with a lethal dose of the 9L-E glioma cells implanted intracranially into rats.

The B16-E cells and 9L-E cells were cloned to homogeneity and shown to express human EGFR, as assayed by flow cytometry. To ensure that the heterologous expression of the human EGFR protein did not result in immune rejection of the tumors in the absence of vaccine administration, the transfected B16-E were first determined to be capable of forming subcutaneous tumors in mice (data not shown). The transfected 9L-E cells formed tumors subcutaneously and intracranially in rats (data not shown). Now the stage was set for testing the efficacy of EGFR-tm VAX yeast vaccine for protecting animals against B16-E tumor challenge in mice and 9L-E tumor challenge in rats.

Preliminary vaccine challenge studies were designed to determine whether subcutaneous vaccination with EGFR-tm VAX is efficacious for protecting animals against challenge with a lethal dose of the B16-E melanoma tumor cells implanted subcutaneously. This approach represents one of the inventors' standard measure for the utility of a new target tumor antigen to be effective for eliciting tumor cell killing. This study demonstrated that animals vaccinated with EGFR-tm VAX are protected against B16-E tumor challenge (4/6 animals are tumor-free), as compared to mock-immunized animals (1/6 animals are tumor-free) (data not shown). These results validate that EGFR serves as an appropriate antigen for eliciting cell-mediated immune responses, and that the EGFR-tm vaccine triggers protective immune responses against tumor challenge. Therefore, the next step was to test the efficacy of EGFR-tm VAX against intracranial challenge with 9L-E gliomas in rats.

The inventors also demonstrated in the experiment above that the yeast-based vaccine, when administered intranasally (i.n.), provides equivalent protection as subcutaneous immunization of the vaccine against subcutaneous melanoma tumor challenge (data not shown). Therefore, the next experiment tested whether the yeast-based immunotherapeutic EGFR-VAX product, which was demonstrated to elicit protective immune responses against a subcutaneous B16 melanoma tumor challenge, would provide immunotherapeutic protection against an intracranial tumor challenge.

The efficacy of the EGFR-tm VAX and the impact of route of administration was further tested by intracranial challenge with glioma tumor cells in the rat model. Animals (8 animals per group) were immunized with ~20 million yeast cells expressing hEGFR (EGFR-vax) or yeast (vector alone) by the intranasal (i.n.) or subcutaneous (s.c.) route on days 0, 7, 21. Immunized animals were challenged by intracranial administration of 1,250 cells of the untransfected 9L rat glioma (9L alone) or 9L expressing hEGFR. Rat body weights were monitored daily, where loss of body weight was indicative of impending animal mortality.

Figure 4:
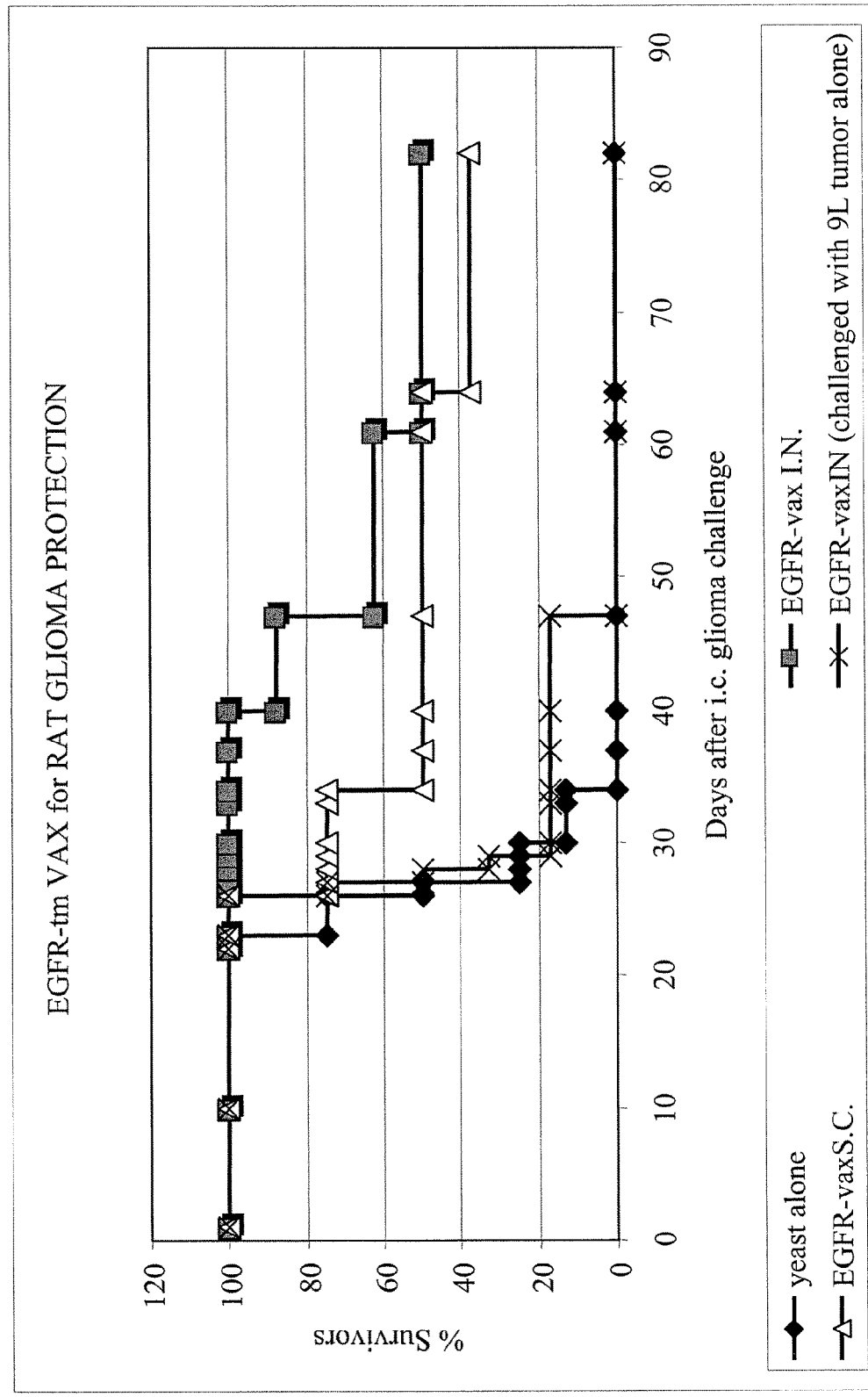
FIG. 4 is a survival graph showing that the yeast-based vaccine expressing EGFR (EGFR-tm VAX) protects against challenge with intracranial tumors expressing EGFR when administered subcutaneously and intranasally.

The results (FIG. 4) demonstrated that 50% of the animals immunized with EGFR-VAX yeast were completely protected against lethal intracranial tumor challenge with the rat 9L glioma expressing the tumor antigen, but none of the animals rejected the growth of tumors that lack the tumor antigen (i.e., the vaccine induces antigen-specific immunity). In addition, the remaining EGFR-VAX-immunized animals that succumbed to the lethal challenge still demonstrated extended survival time as compared to control animals.

Furthermore, the statistically significant improvement in survival of animals that were immunized intranasally as compared to subcutaneously is both intriguing and surprising, and reproduces the data that were described above (see Example 2) regarding protection against intracranial (melanoma) tumor challenge in mice.

Because this rat intracranial tumor challenge model is considered to most closely reflect human glioma, positive data with these studies provide excellent pre-clinical data for moving into a clinical trial. Additional studies can include dose ranging, schedule, surgical re-section studies, and re-challenge of 9L-E survivors with 9L tumors to examine whether the immune system is now "educated" with regard to additional (unknown) tumor antigens in 9L gliomas, as well as testing of yeast vehicles expressing the EGFR-vIII mutant protein, and will establish a basis to begin manufacturing of clinical grade vaccine product.

The data described above indicate that while multiple routes of immunization may be effective for destroying tumors in the periphery, the yeast-based vaccines of the present invention are particularly efficacious for priming effector cells that may be unique to the lung. Since the yeast-based vaccine can prime unique effector cell precursors, the immune cells activated by intranasal immunization may be particularly effective for crossing the blood-brain barrier to influence the course of intracranial tumor growth. Therefore, the route of immunization may be a critical and previously unappreciated component in the design of an effective yeast-based vaccine for brain tumors. Because the yeast-based vaccine is extremely facile for multiple routes of immunization the vaccine holds the promise to uniquely provoke highly specialized immune responses with heretofore underappreciated potential for the treatment of some cancers.

Example 4

The following example demonstrates the use of a yeast-based vaccine comprising a cancer antigen to treat renal cancer in vivo.

In 2001, renal cell cancer (RCC) will be diagnosed in approximately 31,800 individuals in the United States, with 11,600 deaths; this represents 2 to 3 percent of all cancers and 2 percent of all deaths from neoplasms. Although patients traditionally presented with the triad of hematuria, abdominal mass, pain, and weight loss, fewer currently diagnosed patients have these symptoms because of the increased frequency of incidental diagnosis. Many patients are diagnosed with disease that, although potentially curable by surgery, will relapse because cells have already reached the vascular system. Moreover, therapy for metastatic RCC is extremely limited. Hormonal and chemotherapeutic approaches produce <10% response rates and no appreciable change in survival. However, there has been a long-standing interest in the use of immunologic treatment for the disease. In addition to the rare instances of spontaneous regression, both α-interferon and interleukin-2 have shown "significant" activity with a definite minority of patients responding to treatment, some with complete remissions. Although there are few prospective randomized trials, a recent abstract from the Cytokine Working Group documented an 8% complete response rate and 25% overall response rate to high-dose IL-2 compared with about half the response rate with outpatient subcutaneous IL-2/α-interferon. Overall, while clearly showing activity against RCC, approaches used to date have lacked both specificity for the disease and potency.

Over 60% of RCCs carry inactivating mutations in VHL, which appears to act as a "gatekeeper" gene for RCC, analogous to the role of APC in colon cancer. The protein encoded by VHL is an essential component of an E3 ubiquitin-ligation (SCF) complex, known as VHL/elonginCB/Cul-2 (VCB), which targets particular proteins for destruction by the 26S proteasome. Since many VHL mutations result in missense or frameshifted proteins, novel epitopes will be generated that should be recognized as tumor-specific antigens. The following experiments tested the hypothesis that mutant VHL proteins in RCCs can be targeted for immune responses after incorporation into a novel yeast-based vaccine of the present invention.

There are no comparable mutated VHL mediated tumors in mice. Therefore, the present inventors used the known human VHL sequence (SEQ ID NO:16) as well as cloned mouse VHL (SEQ ID NO:17) to prepare expression constructs encoding murine VHL sequences which are either wild-type or carry two specific mutations affecting Y98 or R167 (with respect to the murine sequence of SEQ ID NO:17). Mutations in these two positions correspond to hot spots frequently found in human tumors. Tyrosine 98 forms a surface exposed binding site for VHL targets such as HIF1α while arginine 167 is important for stabilization of the alpha helix H1. Both of these residues are significantly exposed to solvent and are likely to be accessible for immune system recognition. As shown in the BLAST comparison below, human and murine VHL amino acid sequences are nearly identical from position 58 through 190, including these two hot spots.

```
         58                            Tyrosine98                117
hVHL:RPRPVLRSVNSREPSQVIFCNRSPRVVLPVWLNFDGEPQPYPTLPPGTGRRIHSYRGHLW  SEQ ID NO: 16
mVHL:RPRPVLRSVNSREPSQVIFCNRSPRVVLPLWLNFDGEPQPYPILPPGTGRRIHSYRGHLW  SEQ ID NO: 17
    24                                                          83

118                                   Arginine167      177
hVHL:LFRDAGTHDGLLVNQTELFVPSLNVDGQPIFANITLPVYTLKERCLQVVRSLVKPENYRR
mVHL:LFRDAGTHDGLLVNQTELFVPSLNVDGQPIFANITLPVYTLKERCLQVVRSLVKPENYRR
    84                                                         143

178                          211
hVHL:LDIVRSLYEDLEDHPNVQKDLERLTQERIAHQRM
mVHL:LDIVRSLYEDLEDYPSVRKDIQRLSQEHLESQHL
        144                         177
```

Therefore, results obtained with these murine constructs provide a reasonably accurate estimate of the effectiveness in human RCC. Y98 is most frequently mutated into histidine, while R167 is typically mutated to glutamine or tryptophane. R167 is also affected by frame shift mutations; an insertion of a single G residue within the R 167 codon will generate a novel frame shifted peptide (REPSQA) followed by a STOP codon (TGA). The present inventors generated both a histidine missense mutation at Y98 (Y98H) and a frameshift mutation at R167 (R167fr) to create potentially immunogenic mutant VHL proteins that recapitulate features of known VHL mutations. The frame shifted VHL protein will express a larger novel epitope and may thus be more immunogenic. The single missense Y98H mutation will be a more stringent test of this approach since it entails a single amino acid change. These mutations were introduced into the full-length mVHL sequence using both a site-specific mutagenesis protocol and PCR. Briefly, the R133 mutation was created using specific PCR primers to introduce the mutation and premature stop codon. This mutant, as well as wild-type (WT) VHL, was cloned into the yeast expression vector, pYEX-BX used for yeast expression and into a mammalian expression vector pUP for transfection and expression in melanoma cells. The Y64 point mutation was created using a site-specific mutagenesis protocol from Clontech that has shown previous success.

The inserts were cloned into the yeast expression vector pYEX-BX and into the mammalian expression vector pUP for transfection and expression in melanoma cells. To achieve this goal, the inventors engineered yeast to express the VHL protein and tested the efficacy of the various vaccine formulations in mice. The pYEX-BX plasmid contains a copper-inducible promoter that will permit controlled induction of murine VHL protein after transformation of S. cerevisiae.

The expression vectors harboring the VHL genes under control of the constitutive CMV early promoter were transfected into B16 melanoma cells. The cell lines grew in vitro and grew as tumors when injected into mice, confirming that the mutated VHL constructs were not by themselves immunogenic or otherwise lethal to the transfected cells. The first vaccination/tumor challenge experiment consisted of eighteen 6 week old C57B6 mice being immunized by subcutaneous injection on day 0 and day 7 with 20×10$^6$ yeast expressing the R133 truncation mutant (VHLtrunc). On day 14, the mice were challenged with tumor by subcutaneous injection as follows: 6 mice received 2.5×10$^4$ untransfected B16; 6 mice received 2.5×10$^4$ B16 expressing VHLwt; 6 mice received 2.5×10$^4$ B16 expressing VHL VHLtrunc. The mice were evaluated for tumor growth 21 days post challenge. The results of this experiment are outlined in Table 1 below.

TABLE 1

| Immunization | Tumor Challenge | Tumor Growth (# mice with tumors) |
|---|---|---|
| mVHLtrunc VAX | B16 | 5/6 |
| mVHLtrunc VAX | B16 VHLwt | 5/6 |
| mVHLtrunc VAX | B16 VHLtrunc | 0/6 |

These results showed that while the VHLtrunc vaccine (targeting a unique 9 amino acids prior to truncation) provided protection from the B16 VHL tMut tumor challenge, the vaccine did not protect mice challenged with untransfected B16 or B16 VHLwt. Therefore, the vaccination protocol induces a powerful immune response, but this response may be limited only to the antigen against which the animals were vaccinated. However, because this truncated mutant generates a large sequence difference from wild type VHL, it is possible that a more subtle mutation (i.e., only one residue) may produce an immune response to both mutant and wild type.

In a second immunization/challenge experiment (Table 2), mice were immunized with either the wild-type VHL vaccine (mVHLwtVAX) or with the truncated mutant VHL vaccine described above (mVHLtrunc VAX). The mice were divided into groups and challenged with untransfected B16, B16 expressing wildtype VHL or B16 expressing the mutated VHL, as described in the first experiment above. Results showed that again, immunization with the truncated VHL vaccine resulted in protection from tumor challenge, and again confirmed that these mice were not protected against challenge with wildtype tumor. Mice immunized with the wildtype tumor were not protected against challenge with the wildtype tumor, indicating that the vaccine did not break tolerance to the wildtype protein. However, when challenged with the mutated VHL-expressing tumor, 50% of the mice immunized with wild-type protein were protected, indicating that the mutated VHL was recognized to some extent by the murine immune system. Given the specificity and efficacy of the yeast-based vaccine in these experiments, it will be a relatively simple task to generate yeast targeting the most common mutations in humans, paving the way for a potential immunization approach as a therapeutic vaccine in humans.

TABLE 2

| Immunization | Tumor Challenge | Tumor Growth (# mice with tumors) |
|---|---|---|
| mock | B16 | 3/3 |
|  | B16 VHLwt | 3/3 |
|  | B16 VHLtrunc | 2/3 |
| mVHLwt VAX | B16 | 5/6 |
|  | B16 VHLwt | 5/6 |
|  | B16 VHLtrunc | 3/6 |

TABLE 2-continued

| Immunization | Tumor Challenge | Tumor Growth (# mice with tumors) |
|---|---|---|
| mVHLtrunc VAX | B16 | 5/6 |
| | B16 VHLwt | 4/5 |
| | B16 VHLtrunc | 0/6 |

Example 5

The following example demonstrates the use of a yeast-based vaccine comprising a cancer antigen to treat breast cancer in vivo.

Most patients with early-stage cancers of solid organs, including lung, breast, and colon, can be cured by surgical removal of the primary tumor. Unfortunately, many patients present or relapse with hematogenous metastases which, with rare exceptions, cannot be cured by currently available modalities, including surgery, radiation therapy, chemotherapy, or allogeneic stem cell transplantation (alloSCT). Likewise, although newer engineered cancer vaccines show significant potency in animal models of recently established disease, once the tumor has been established for more than 5 days or metastases have occurred, vaccines are generally ineffective as single agents (Borello et al., 2000, *Blood* 95:3011-3019) This is in part because tumor establishment is typically associated with induction of tolerance to tumor antigens, which must be broken to achieve successful therapy (Ye et al., 1994, *Proc. NatL Acad. Sci. USA.* 91:3916-3920; Staveley-O'Carroll et al., 1998, *Proc. Natl. Acad. Sci. USA* 95:1178-1183). Vaccination after myeloablative alloSCT has produced incremental improvements but is still unable to affect tumors established for more than 3 days (Anderson et al., 2000, *Blood* 95:2426-2433). Luznik et al., supra, incorporated herein in its entirety, recently reported in a mouse breast cancer model that vaccination after a nonmyeloablative allogeneic stem cell transplantation (NST) protocol that achieves stable mixed bone marrow chimerism generates significantly enhanced tumor-specific immune responses capable of eliminating metastases 2 weeks after establishment of the primary tumor without inducing graft-versus-host disease (GVHD). The significantly enhanced efficacy of this strategy relative to vaccination alone or vaccination after either autologous SCT or full alloSCT depends on the action of both host and donor immune systems, which interact in the setting of mixed chimerism.

Figure 5:
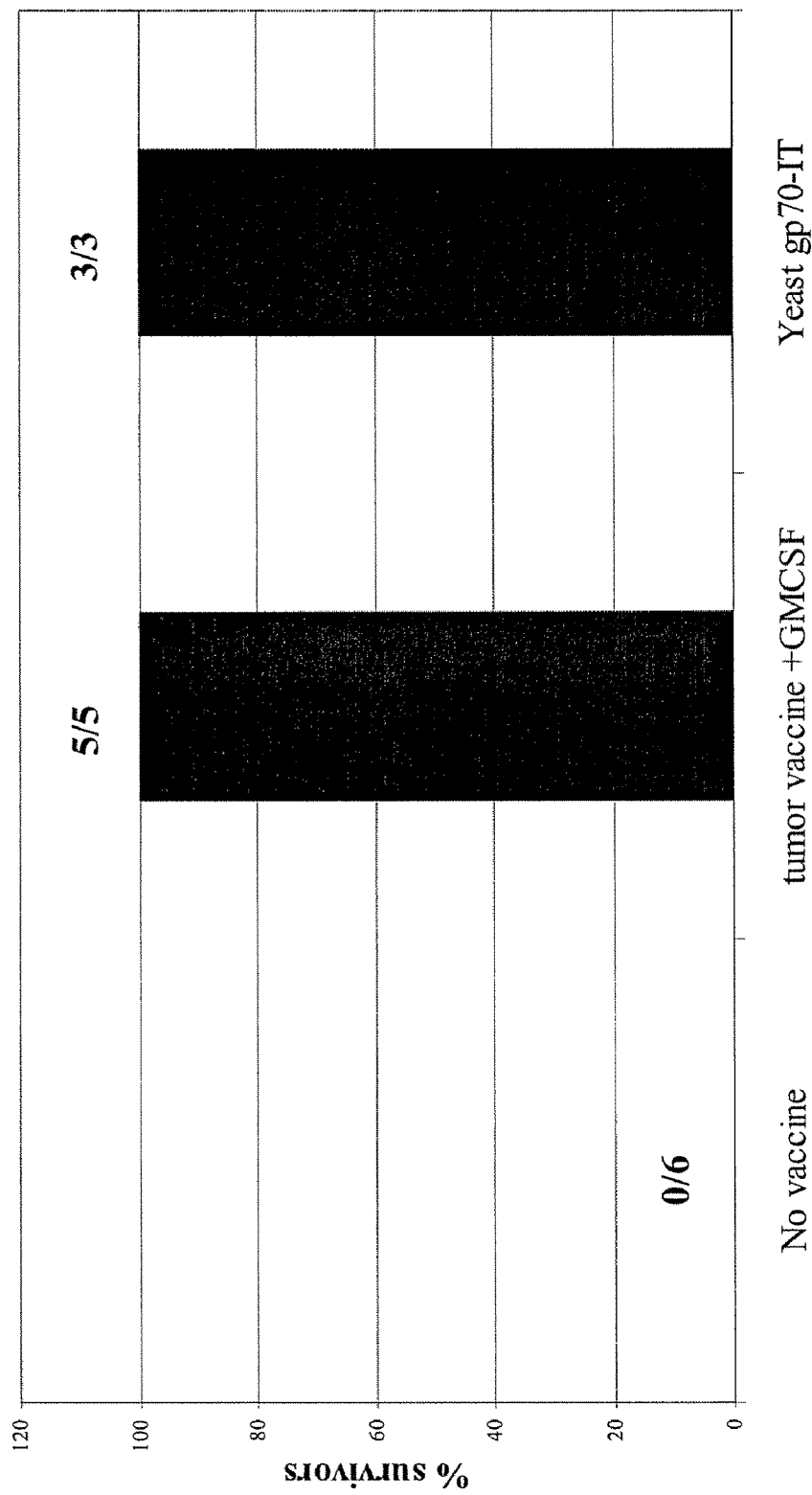
FIG. 5 is a bar graph showing that vaccination with a yeast-based vaccine expressing a breast tumor antigen in conjunction with non-myeloablative allogeneic stem cell transplantation protects against tumor challenge.

In the experiments of Luznik et al., the vaccine that was administered consisted of irradiated autologous tumor cells mixed with granulocyte-macrophage colony stimulating factor (GM-CSF). In the following experiment, the present inventors showed that a yeast-based vaccine could substitute for the use of irradiated autologous tumor cells mixed with cells producing GM-CSF in the same animal model with equally efficacious results. In brief, the present inventors generated a yeast-based vaccine comprised of *Saccharomyces cerevisiae* yeast transduced with a yeast expression vector encoding the gp70 protein of the mouse mammary tumor virus (MMTV) under the control of the CUP1 promoter (Yeast gp70-IT). The gp70 protein is expressed in spontaneous breast cancers that arise in Balb/c mice that are infected with MMTV. Following the protocol described by Luznik et al., Balb/c mice were injected subcutaneously with 10,000 4T1 tumor cells (Balb/c-derived spontaneous breast cancer cells that express MMTV gp70) on day 0. The subcutaneous tumor was resected on day 13, prior to nonmyeloablative allogeneic stem cell transplantation (NST) from MHC-compatible B10.D2 donors. NST consisted of 200 cGy TBI on day 13, 10 million donor marrow cells intravenously on day 14, and cyclophosphamide 200 mg/kg intraperitoneally on day 17. Mice receiving B10.D2 marrow then received either: (a) 20 million B10.D2 splenocytes on day 28 with no further treatment (No vaccine); (b) 20 million B10.D2 splenocytes on day 28 plus autologous tumor vaccine on day 31 ($10^6$ irradiated 4T1 tumor cells mixed with $5 \times 10^5$ B78H1/GM-CSF, a GM-CSF-secreting, MHC-negative bystander cell line), or (c) 20 million B10.D2 splenocytes on day 28 plus the Yeast-based gp70-IT vaccine of the present invention on day 31. As is readily apparent in FIG. 5, the yeast-based vaccine of the present invention induced protection against fatal tumor recurrence indistinguishable from protection induced by autologous tumor cells producing GM-CSF. The clinical usefulness of the yeast-based vaccine approach of the present invention, as compared to using patient autologous tumor cells admixed with a bystander cell line producing GM-CSF, should be readily appreciated, and includes, but is not limited to, the advantages of broader patient applicability, reduced variability of results, enhanced ability to design the vaccinating antigen, enhanced safety, lack of necessity to include biological modifiers such as GM-CSF in the vaccine, etc.

Example 6

The following example demonstrates the use of a yeast-based vaccine comprising a cancer antigen to treat a melanoma in vivo.

In this experiment, referring to Table 3, 5 groups of 5 mice each were used. In Group A, mice received injections of PBS at 4 weeks and 2 weeks prior to tumor challenge, and $50 \times 10^6$ yeast-based hMART-1 vaccine (yeast vehicle expressing human MART-1) at days 10 and 17 after tumor challenge. In Group B, mice received injections of $50 \times 10^6$ yeast-based hMART-1 vaccine at 4 weeks and 2 weeks prior to tumor challenge and at 10 and 17 days after tumor challenge. Group C mice received PBS at 4 weeks and 2 weeks prior to tumor challenge and no administrations after tumor challenge. Group D mice received injections of $50 \times 10^6$ yeast-based hMART-1 vaccine at 4 weeks and 2 weeks prior to tumor challenge and no administrations after tumor challenge. Group E mice received $50 \times 10^6$ yeast-based EGFR vaccine (yeast vehicles expressing EGFR) at 4 weeks and 2 weeks prior to tumor challenge and no administrations after tumor challenge. At day 0, all mice received a tumor challenge of D16 melanoma cells delivered subcutaneously. Mice in Groups A-D received 50,000 D16 melanoma cells, which expressed endogenous mouse MART-1 (the cells were not transfected with human MART-1), and the mice in Group E received 50,000 D16 melanoma cells that had been transfected with EGFR.

TABLE 3

| | hMART-1 Vaccination | | | | |
|---|---|---|---|---|---|
| | −4 wk | −2 wk | 0 | D10 | D17 |
| A (5) | PBS | PBS | 50K B16 | 2-8OD | 2-8OD |
| B (5) | 2OD | 2OD | 50K B16 | 2OD | 2OD |
| C (5) | PBS | PBS | 50K B16 | | |
| D (5) | 2OD | 2OD | 50K B16 | | |
| E (5) | 2OD EGFR | 2OD EGFR | 25-50K B16/EGFR | | |

Figure 6:
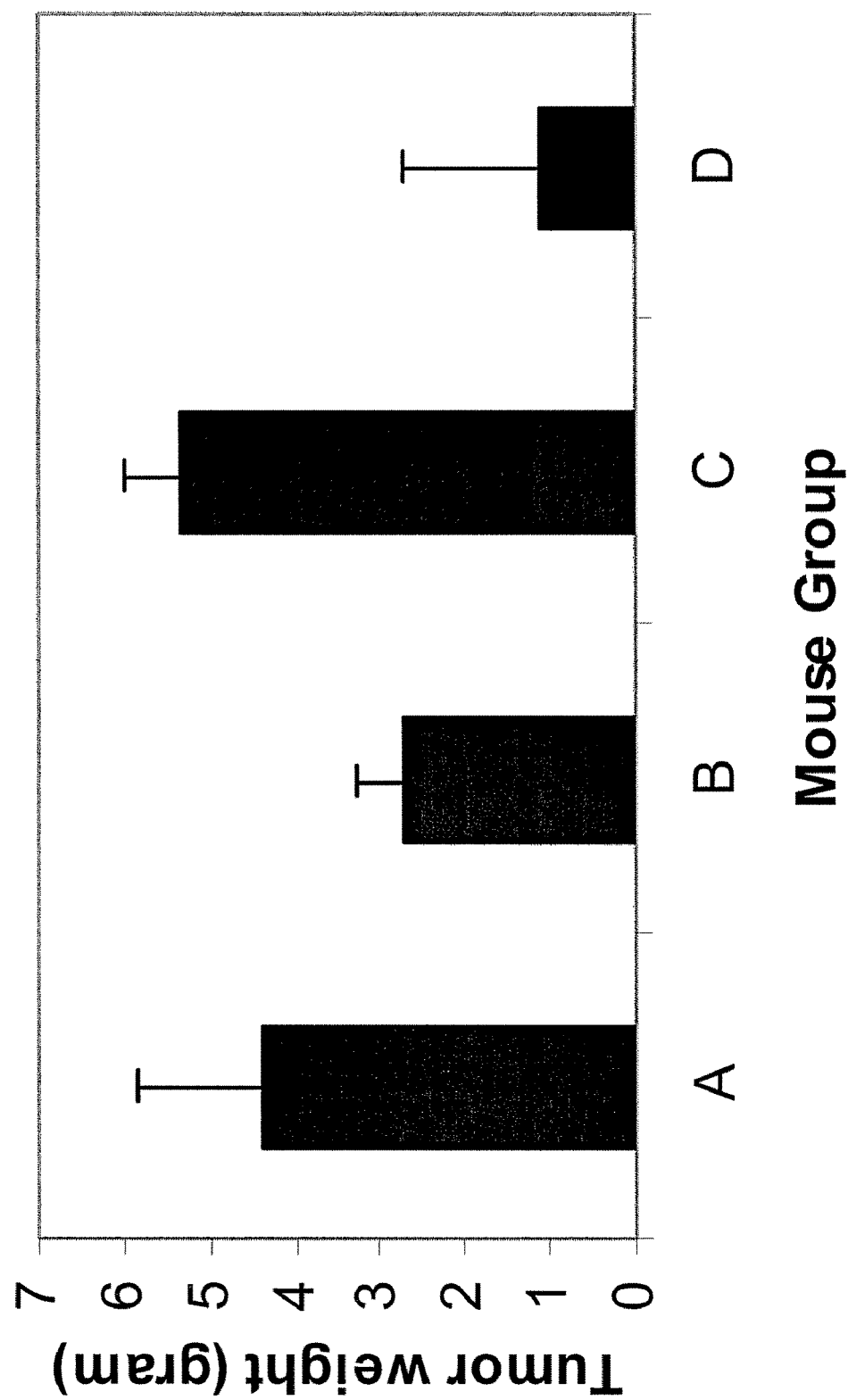
FIG. 6 is a bar graph showing that vaccination with a yeast-based vaccine expressing a melanoma antigen protects against tumor challenge with melanoma tumors expressing the antigen.

The results are shown in FIG. 6. Mice in Groups B (immunized both before and after tumor challenge) and D (immunized before tumor challenge) showed significant reduction in tumor burden, demonstrating that the yeast vaccine expressing a melanoma antigen is effective against melanoma tumors, even across species.

Example 7

The following example demonstrates the construction of fusion proteins for expression in a yeast vehicle of the invention, wherein the fusion proteins comprise multiple immunogenic domains and multiple mutations of the same antigen.

The nucleotide and amino acid sequence for a variety of Ras family members are well known in the art. SEQ ID NO:2 is the nucleic acid sequence encoding human K-ras (also known in GenBank Accession No. NM_033360). SEQ ID NO:2 encodes human K-ras, represented herein as SEQ ID NO:3. SEQ ID NO:4 is the nucleic acid sequence encoding murine K-ras (also known in GenBank Accession No. NM_021284). SEQ ID NO:4 encodes murine K-ras, represented herein as SEQ ID NO:5. SEQ ID NO:6 is the nucleic acid sequence encoding human H-ras (also known in GenBank Accession No. NM_005343). SEQ ID NO:6 encodes human H-ras, represented herein as SEQ ID NO:7. SEQ ID NO:8 is the nucleic acid sequence encoding murine H-ras (also known in GenBank Accession No. NM_008284). SEQ ID NO:8 encodes murine H-ras, represented herein as SEQ ID NO:9. SEQ ID NO:10 is the nucleic acid sequence encoding human N-ras (also known in GenBank Accession No. NM_002524). SEQ ID NO:10 encodes human N-ras, represented herein as SEQ ID NO: 11. SEQ ID NO: 12 is the nucleic acid sequence encoding murine N-ras (also known in GenBank Accession No. NM_010937). SEQ ID NO:12 encodes human N-ras, represented herein as SEQ ID NO:13.

Figure 7:
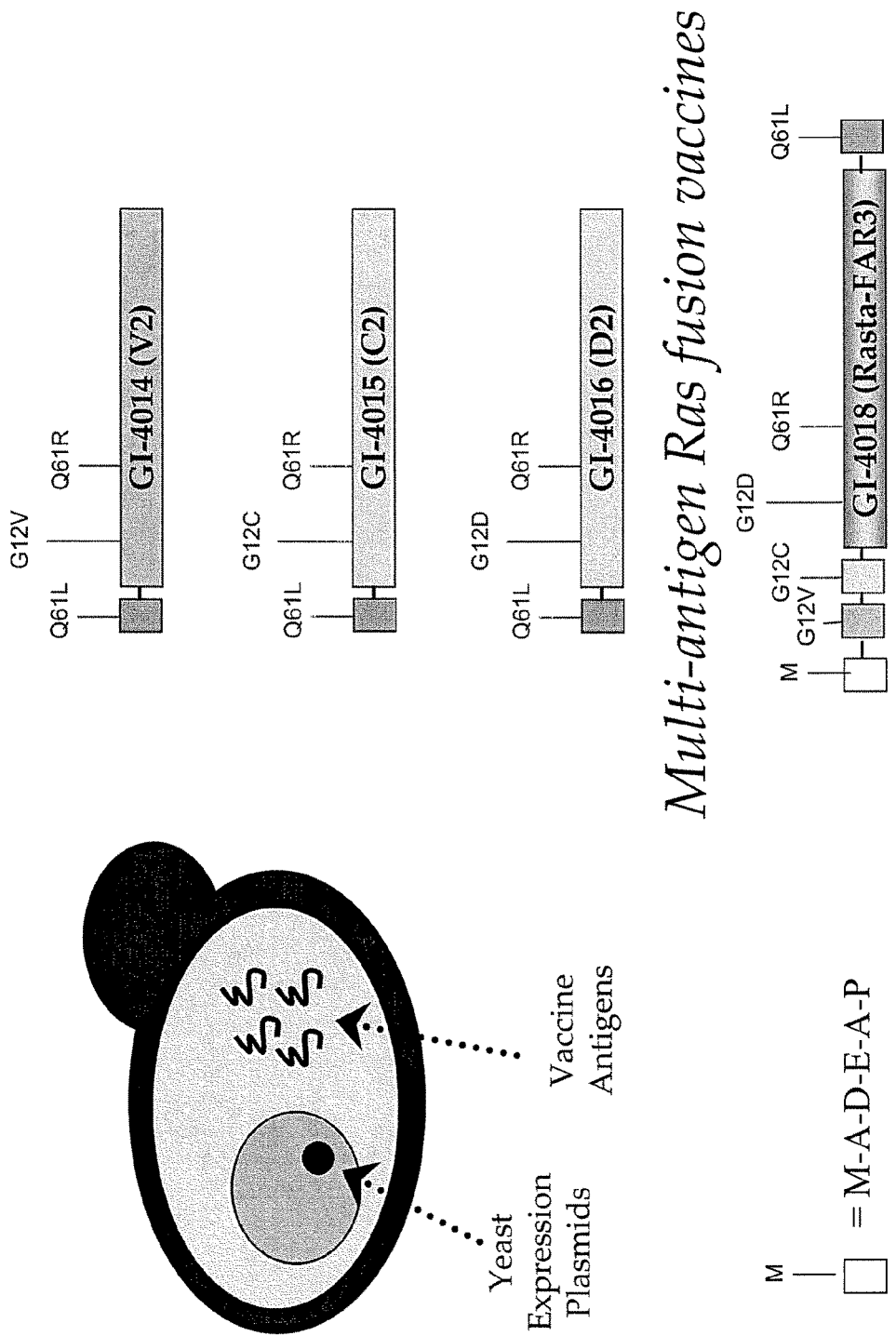
FIG. 7 is a schematic drawing showing the construction of various mutant Ras fusion proteins for use in a yeast-based vaccine of the invention.

FIG. 7 is a schematic drawing illustrating examples of fusion proteins comprising multiple antigenic/immunogenic domains for use in a yeast-based vaccine of the present invention. In these exemplary fusion constructs, amino acid positions 3-165 of a K-Ras protein (positions 3-165 of SEQ ID NO:3) were used, which are also equivalent amino acids in N-Ras and H-Ras (i.e., one could use positions 3-165 of N-Ras or H-Ras and achieve the same result). This sequence was then mutated at position 12 to substitute a valine, cysteine or aspartic acid residue for the glycine that normally occurs in this position (see GI-4014, GI-4015 and GI-4016, respectively), and at position 61 to substitute an arginine for the glutamine that normally occurs at this position. A second sequence was fused to (appended to) this sequence. The second sequence is a domain from K-ras spanning amino acid positions 56-69 of SEQ ID NO:3, which includes a mutation at position 61 to substitute a leucine for the glutamine residue that normally occurs at that position. Although these first three sequences are shown with the Q61L domain fused to the N-terminus of the longer sequence, other constructs have been produced in which the order of domains is reversed. The nucleotide and translated amino acid sequence for the construct encoding GI-4014 are represented by SEQ ID Nos:14 and 15, respectively.

FIG. 7 also shows a multi-antigen Ras fusion vaccine (GI-4018), which contains all three of the position 12 mutations described above and both of the position 61 mutations described above. The fusion protein was constructed as follows. A synthetic sequence comprising SEQ ID NO:1 is followed by four polypeptides which include various Ras mutations. The first of the four depicted in FIG. 7 includes residues 3-30 of the N-terminus of K-Ras (SEQ ID NO:3), wherein the amino acid residue at position 12 with respect to SEQ ID NO:3 has been mutated by substitution of a valine for the glycine that naturally occurs at this position. The second of the four domains includes amino acid residues 3-39 of SEQ ID NO:3), wherein the amino acid residue at position 12 with respect to SEQ ID NO:3 has been mutated by substitution of a cysteine for the glycine that naturally occurs at this position. The third of the four domains consists of amino acid positions 3-165 of SEQ ID NO:3), which contains a substitution of an aspartic acid for the glycine that normally occurs at position 12 and a substitution of an arginine for the glutamine that normally occurs at position 61. The fourth of the four domains is a domain from K-ras spanning amino acid positions 56-69 of SEQ ID NO:3, which includes a mutation at position 61 to substitute a leucine for the glutamine residue that normally occurs at that position. Again, although the domains are depicted in this order in FIG. 7, it is to be understood that the order of domains can be reorganized as desired.

This example is simply intended to be illustrative of how antigen constructs useful in the present invention can be constructed. Similar strategies using domains from different antigens, multiple domains from the same antigen, or repeated domains with different mutations, can be used for other antigens. This type of construct is particularly useful when it is desirable to encompass several different mutations and/or combinations of mutations that may occur at a single position in the antigen in nature, in a single vaccine construct.

All references cited herein are incorporated by reference in their entireties.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed is:

1. A method to increase survival or reduce tumor burden in a patient that has a cancer that expresses carcinoembryonic antigen (CEA), comprising administering to a patient with a cancer that expresses CEA an immunotherapy composition consisting of a yeast vehicle that expresses a full-length CEA protein;
   wherein the CEA protein does not comprise a synthetic peptide linked to the N-terminus of the CEA protein consisting of at least two amino acid residues that are heterologous to the protein and that stabilizes the expression of the protein in the yeast vehicle or prevents posttranslational modification of the expressed protein; and
   wherein administration of the composition to the patient increases survival of the patient or reduces tumor burden in the patient.

2. The method of claim 1, wherein the CEA protein is a mutated CEA.

3. The method of claim 2, wherein the mutated CEA contains an amino acid substitution.

4. The method of claim 1, wherein the yeast vehicle is selected from the group consisting of a whole yeast and a yeast spheroplast.

5. The method of claim 1, wherein the yeast vehicle is a whole yeast.

6. The method of claim 1, wherein the yeast vehicle is a whole, killed yeast.

7. The method of claim 1, wherein the yeast vehicle is from *Saccharomyces*.

8. The method of claim 1, wherein yeast vehicle is from *Saccharomyces cerevisiae*.

9. The method of claim 1, wherein the composition is administered after surgical resection of a tumor from the patient.

10. The method of claim 1, wherein the composition is administered in combination with another therapeutic treatment for cancer.

11. The method of claim 10, wherein the therapeutic treatment for cancer is chemotherapy.

12. The method of claim 1, wherein the composition is administered by subcutaneous injection.

13. A method to increase survival or reduce tumor burden in a patient that has a cancer that expresses carcinoembryonic antigen (CEA), comprising administering to a patient with a cancer that expresses CEA, an immunotherapy composition consisting of a CEA immunogen consisting of a yeast vehicle that expresses a full-length CEA protein, wherein administration of the composition to the patient increases survival of the patient or reduces tumor burden in the patient.

14. The method of claim 13, wherein the CEA protein is mutated.

15. The method of claim 13, wherein the yeast vehicle is a whole, killed yeast.

16. The method of claim 13, wherein yeast vehicle is from *Saccharomyces cerevisiae*.

17. A method to increase survival or reduce tumor burden in a patient that has a cancer that expresses carcinoembryonic antigen (CEA), comprising administering to a patient with a cancer that expresses CEA: (a) chemotherapy; and (b) an immunotherapy composition consisting of a yeast vehicle from *Saccharomyces* that expresses a full-length CEA protein, wherein administration of the composition to the patient increases survival of the patient or reduces tumor burden in the patient.

18. The method of claim 17, wherein the step of administering occurs after surgical resection of a tumor from the patient.

19. The method of claim 17, wherein the CEA antigen is mutated.

20. The method of claim 17, wherein the yeast vehicle is a whole, killed yeast.

21. The method of claim 17, wherein yeast vehicle is from *Saccharomyces cerevisiae*.

22. The method of claim 13, wherein the mutated CEA contains an amino acid substitution.

23. The method of claim 17, wherein the mutated CEA contains an amino acid substitution.

* * * * *

SEQUENCE LISTING

```
<160> NUMBER OF SEQ ID NOS: 17

<210> SEQ ID NO 1
<211> LENGTH: 6
<212> TYPE: PRT
<213> ORGANISM: Artificial sequence
<220> FEATURE:
<223> OTHER INFORMATION: synthetic peptide

<400> SEQUENCE: 1

Met Ala Asp Glu Ala Pro
1               5
```

<210> SEQ ID NO 2
<211> LENGTH: 570
<212> TYPE: DNA
<213> ORGANISM: Homo sapiens
<220> FEATURE:
<221> NAME/KEY: CDS
<222> LOCATION: (1)..(570)

<400> SEQUENCE: 2

```
atg act gaa tat aaa ctt gtg gta gtt gga gct ggt ggc gta ggc aag      48
Met Thr Glu Tyr Lys Leu Val Val Val Gly Ala Gly Gly Val Gly Lys
1               5                   10                  15 agt gcc ttg acg ata cag cta att cag aat cat ttt gtg gac gaa tat      96
Ser Ala Leu Thr Ile Gln Leu Ile Gln Asn His Phe Val Asp Glu Tyr
            20                  25                  30 gat cca aca ata gag gat tcc tac agg aag caa gta gta att gat gga     144
Asp Pro Thr Ile Glu Asp Ser Tyr Arg Lys Gln Val Val Ile Asp Gly
        35                  40                  45 gaa acc tgt ctc ttg gat att ctc gac aca gca ggt caa gag gag tac     192
Glu Thr Cys Leu Leu Asp Ile Leu Asp Thr Ala Gly Gln Glu Glu Tyr
    50                  55                  60 agt gca atg agg gac cag tac atg agg act ggg gag ggc ttt ctt tgt     240
Ser Ala Met Arg Asp Gln Tyr Met Arg Thr Gly Glu Gly Phe Leu Cys
65                  70                  75                  80 gta ttt gcc ata aat aat act aaa tca ttt gaa gat att cac cat tat     288
Val Phe Ala Ile Asn Asn Thr Lys Ser Phe Glu Asp Ile His His Tyr
                85                  90                  95 aga gaa caa att aaa aga gtt aag gac tct gaa gat gta cct atg gtc     336
Arg Glu Gln Ile Lys Arg Val Lys Asp Ser Glu Asp Val Pro Met Val
            100                 105                 110 cta gta gga aat aaa tgt gat ttg cct tct aga aca gta gac aca aaa     384
Leu Val Gly Asn Lys Cys Asp Leu Pro Ser Arg Thr Val Asp Thr Lys
        115                 120                 125 cag gct cag gac tta gca aga agt tat gga att cct ttt att gaa aca     432
Gln Ala Gln Asp Leu Ala Arg Ser Tyr Gly Ile Pro Phe Ile Glu Thr
    130                 135                 140 tca gca aag aca aga cag aga gtg gag gat gct ttt tat aca ttg gtg     480
Ser Ala Lys Thr Arg Gln Arg Val Glu Asp Ala Phe Tyr Thr Leu Val
145                 150                 155                 160 agg gag atc cga caa tac aga ttg aaa aaa atc agc aaa gaa gaa aag     528
Arg Glu Ile Arg Gln Tyr Arg Leu Lys Lys Ile Ser Lys Glu Glu Lys
                165                 170                 175 act cct ggc tgt gtg aaa att aaa aaa tgc att ata atg taa             570
Thr Pro Gly Cys Val Lys Ile Lys Lys Cys Ile Ile Met
            180                 185
```

<210> SEQ ID NO 3
<211> LENGTH: 189
<212> TYPE: PRT
<213> ORGANISM: Homo sapiens

<400> SEQUENCE: 3

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
```

```
                65                    70                   75                   80
          Val Phe Ala Ile Asn Asn Thr Lys Ser Phe Glu Asp Ile His His Tyr
                                85                   90                   95
          Arg Glu Gln Ile Lys Arg Val Lys Asp Ser Glu Asp Val Pro Met Val
                           100                  105                  110
          Leu Val Gly Asn Lys Cys Asp Leu Pro Ser Arg Thr Val Asp Thr Lys
                       115                  120                  125
          Gln Ala Gln Asp Leu Ala Arg Ser Tyr Gly Ile Pro Phe Ile Glu Thr
                   130                  135                  140
          Ser Ala Lys Thr Arg Gln Arg Val Glu Asp Ala Phe Tyr Thr Leu Val
          145                  150                  155                  160
          Arg Glu Ile Arg Gln Tyr Arg Leu Lys Lys Ile Ser Lys Glu Glu Lys
                           165                  170                  175
          Thr Pro Gly Cys Val Lys Ile Lys Lys Cys Ile Ile Met
                       180                  185

<210> SEQ ID NO 4
<211> LENGTH: 567
<212> TYPE: DNA
<213> ORGANISM: Mus musculus
<220> FEATURE:
<221> NAME/KEY: CDS
<222> LOCATION: (1)..(567)

<400> SEQUENCE: 4 atg act gag tat aaa ctt gtg gtg gtt gga gct ggt ggc gta ggc aag      48
Met Thr Glu Tyr Lys Leu Val Val Val Gly Ala Gly Gly Val Gly Lys
 1               5                   10                  15 agc gcc ttg acg ata cag cta att cag aat cac ttt gtg gat gag tac      96
Ser Ala Leu Thr Ile Gln Leu Ile Gln Asn His Phe Val Asp Glu Tyr
             20                  25                  30 gac cct acg ata gag gac tcc tac agg aaa caa gta gta att gat gga     144
Asp Pro Thr Ile Glu Asp Ser Tyr Arg Lys Gln Val Val Ile Asp Gly
         35                  40                  45 gaa acc tgt ctc ttg gat att ctc gac aca gca ggt caa gag gag tac     192
Glu Thr Cys Leu Leu Asp Ile Leu Asp Thr Ala Gly Gln Glu Glu Tyr
     50                  55                  60 agt gca atg agg gac cag tac atg aga act ggg gag ggc ttt ctt tgt     240
Ser Ala Met Arg Asp Gln Tyr Met Arg Thr Gly Glu Gly Phe Leu Cys
 65                  70                  75                  80 gta ttt gcc ata aat aat act aaa tca ttt gaa gat att cac cat tat     288
Val Phe Ala Ile Asn Asn Thr Lys Ser Phe Glu Asp Ile His His Tyr
                 85                  90                  95 aga gaa caa att aaa aga gta aag gac tct gaa gat gtg cct atg gtc     336
Arg Glu Gln Ile Lys Arg Val Lys Asp Ser Glu Asp Val Pro Met Val
            100                 105                 110 ctg gta ggg aat aag tgt gat ttg cct tct aga aca gta gac acg aaa     384
Leu Val Gly Asn Lys Cys Asp Leu Pro Ser Arg Thr Val Asp Thr Lys
        115                 120                 125 cag gct cag gag tta gca agg agt tac ggg att ccg ttc att gag acc     432
Gln Ala Gln Glu Leu Ala Arg Ser Tyr Gly Ile Pro Phe Ile Glu Thr
    130                 135                 140 tca gca aag aca aga cag ggt gtt gac gat gcc ttc tat aca tta gtc     480
Ser Ala Lys Thr Arg Gln Gly Val Asp Asp Ala Phe Tyr Thr Leu Val
145                 150                 155                 160 cga gaa att cga aaa cat aaa gaa aag atg agc aaa gat ggg aag aag     528
Arg Glu Ile Arg Lys His Lys Glu Lys Met Ser Lys Asp Gly Lys Lys
                165                 170                 175 aag aag aag aag tca agg aca agg tgt aca gtt atg tga                 567
Lys Lys Lys Lys Ser Arg Thr Arg Cys Thr Val Met
```

<210> SEQ ID NO 5
<211> LENGTH: 188
<212> TYPE: PRT
<213> ORGANISM: Mus musculus

<400> SEQUENCE: 5

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Glu Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Arg Thr Arg Cys Thr Val Met
            180                 185

<210> SEQ ID NO 6
<211> LENGTH: 570
<212> TYPE: DNA
<213> ORGANISM: Homo sapiens
<220> FEATURE:
<221> NAME/KEY: CDS
<222> LOCATION: (1)..(570)

<400> SEQUENCE: 6 atg acg gaa tat aag ctg gtg gtg gtg ggc gcc ggc ggt gtg ggc aag    48
Met Thr Glu Tyr Lys Leu Val Val Val Gly Ala Gly Gly Val Gly Lys
1               5                   10                  15 agt gcg ctg acc atc cag ctg atc cag aac cat ttt gtg gac gaa tac    96
Ser Ala Leu Thr Ile Gln Leu Ile Gln Asn His Phe Val Asp Glu Tyr
            20                  25                  30 gac ccc act ata gag gat tcc tac cgg aag cag gtg gtc att gat ggg   144
Asp Pro Thr Ile Glu Asp Ser Tyr Arg Lys Gln Val Val Ile Asp Gly
        35                  40                  45 gag acg tgc ctg ttg gac atc ctg gat acc gcc ggc cag gag gag tac   192
Glu Thr Cys Leu Leu Asp Ile Leu Asp Thr Ala Gly Gln Glu Glu Tyr
    50                  55                  60 agc gcc atg cgg gac cag tac atg cgc acc ggg gag ggc ttc ctg tgt   240
Ser Ala Met Arg Asp Gln Tyr Met Arg Thr Gly Glu Gly Phe Leu Cys
65                  70                  75                  80 gtg ttt gcc atc aac aac acc aag tct ttt gag gac atc cac cag tac   288
Val Phe Ala Ile Asn Asn Thr Lys Ser Phe Glu Asp Ile His Gln Tyr
                85                  90                  95

```
agg gag cag atc aaa cgg gtg aag gac tcg gat gac gtg ccc atg gtg    336
Arg Glu Gln Ile Lys Arg Val Lys Asp Ser Asp Asp Val Pro Met Val
            100                 105                 110 ctg gtg ggg aac aag tgt gac ctg gct gca cgc act gtg gaa tct cgg    384
Leu Val Gly Asn Lys Cys Asp Leu Ala Ala Arg Thr Val Glu Ser Arg
        115                 120                 125 cag gct cag gac ctc gcc cga agc tac ggc atc ccc tac atc gag acc    432
Gln Ala Gln Asp Leu Ala Arg Ser Tyr Gly Ile Pro Tyr Ile Glu Thr
    130                 135                 140 tcg gcc aag acc cgg cag gga gtg gag gat gcc ttc tac acg ttg gtg    480
Ser Ala Lys Thr Arg Gln Gly Val Glu Asp Ala Phe Tyr Thr Leu Val
145                 150                 155                 160 cgt gag atc cgg cag cac aag ctg cgg aag ctg aac cct cct gat gag    528
Arg Glu Ile Arg Gln His Lys Leu Arg Lys Leu Asn Pro Pro Asp Glu
                165                 170                 175 agt ggc ccc ggc tgc atg agc tgc aag tgt gtg ctc tcc tga            570
Ser Gly Pro Gly Cys Met Ser Cys Lys Cys Val Leu Ser
                180                 185

<210> SEQ ID NO 7
<211> LENGTH: 189
<212> TYPE: PRT
<213> ORGANISM: Homo sapiens

<400> SEQUENCE: 7

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185

<210> SEQ ID NO 8
<211> LENGTH: 570
<212> TYPE: DNA
<213> ORGANISM: Mus musculus
<220> FEATURE:
<221> NAME/KEY: CDS
<222> LOCATION: (1)..(570)

<400> SEQUENCE: 8
```

```
atg aca gaa tac aag ctt gtg gtg gtg ggc gct gga ggc gtg gga aag       48
Met Thr Glu Tyr Lys Leu Val Val Val Gly Ala Gly Gly Val Gly Lys
1               5                   10                  15 agt gcc ctg acc atc cag ctg atc cag aac cac ttt gtg gac gag tat       96
Ser Ala Leu Thr Ile Gln Leu Ile Gln Asn His Phe Val Asp Glu Tyr
                20                  25                  30 gat ccc act ata gag gac tcc tac cgg aaa cag gtg gtc att gat ggg      144
Asp Pro Thr Ile Glu Asp Ser Tyr Arg Lys Gln Val Val Ile Asp Gly
            35                  40                  45 gag aca tgt cta ctg gac tac tta gac aca gca ggt caa gaa gag tat      192
Glu Thr Cys Leu Leu Asp Tyr Leu Asp Thr Ala Gly Gln Glu Glu Tyr
50                  55                  60 agt gcc atg cgg gac cag tac atg cgc aca ggg gag ggc ttc ctc tgt      240
Ser Ala Met Arg Asp Gln Tyr Met Arg Thr Gly Glu Gly Phe Leu Cys
65                  70                  75                  80 gta ttt gcc atc aac aac acc aag tcc ttc gag gac atc cat cag tac      288
Val Phe Ala Ile Asn Asn Thr Lys Ser Phe Glu Asp Ile His Gln Tyr
                85                  90                  95 agg gag cag atc aag cgg gtg aaa gat tca gat gat gtg cca atg gtg      336
Arg Glu Gln Ile Lys Arg Val Lys Asp Ser Asp Asp Val Pro Met Val
            100                 105                 110 ctg gtg ggc aac aag tgt gac ctg gct gct cgc act gtt gag tct cgg      384
Leu Val Gly Asn Lys Cys Asp Leu Ala Ala Arg Thr Val Glu Ser Arg
        115                 120                 125 cag gcc cag gac ctt gct cgc agc tat ggc atc ccc tac att gaa aca      432
Gln Ala Gln Asp Leu Ala Arg Ser Tyr Gly Ile Pro Tyr Ile Glu Thr
130                 135                 140 tca gcc aag acc cgg cag ggc gtg gag gat gcc ttc tat aca cta gtc      480
Ser Ala Lys Thr Arg Gln Gly Val Glu Asp Ala Phe Tyr Thr Leu Val
145                 150                 155                 160 cgt gag att cgg cag cat aaa ttg cgg aaa ctg aac cca ccc gat gag      528
Arg Glu Ile Arg Gln His Lys Leu Arg Lys Leu Asn Pro Pro Asp Glu
                165                 170                 175 agt ggt cct ggc tgc atg agc tgc aaa tgt gtg ctg tcc tga              570
Ser Gly Pro Gly Cys Met Ser Cys Lys Cys Val Leu Ser
            180                 185

<210> SEQ ID NO 9
<211> LENGTH: 189
<212> TYPE: PRT
<213> ORGANISM: Mus musculus

<400> SEQUENCE: 9

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Tyr Leu Asp Thr Ala Gly Gln Glu Glu Tyr
50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125
```

```
Gln Ala Gln Asp Leu Ala Arg Ser Tyr Gly Ile Pro Tyr Ile Glu Thr
        130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185

<210> SEQ ID NO 10
<211> LENGTH: 570
<212> TYPE: DNA
<213> ORGANISM: Homo sapiens
<220> FEATURE:
<221> NAME/KEY: CDS
<222> LOCATION: (1)..(570)

<400> SEQUENCE: 10 atg act gag tac aaa ctg gtg gtg gtt gga gca ggt ggt gtt ggg aaa      48
Met Thr Glu Tyr Lys Leu Val Val Val Gly Ala Gly Gly Val Gly Lys
1               5                   10                  15 agc gca ctg aca atc cag cta atc cag aac cac ttt gta gat gaa tat      96
Ser Ala Leu Thr Ile Gln Leu Ile Gln Asn His Phe Val Asp Glu Tyr
                20                  25                  30 gat ccc acc ata gag gat tct tac aga aaa caa gtg gtt ata gat ggt     144
Asp Pro Thr Ile Glu Asp Ser Tyr Arg Lys Gln Val Val Ile Asp Gly
            35                  40                  45 gaa acc tgt ttg ttg gac ata ctg gat aca gct gga caa gaa gag tac     192
Glu Thr Cys Leu Leu Asp Ile Leu Asp Thr Ala Gly Gln Glu Glu Tyr
    50                  55                  60 agt gcc atg aga gac caa tac atg agg aca ggc gaa ggc ttc ctc tgt     240
Ser Ala Met Arg Asp Gln Tyr Met Arg Thr Gly Glu Gly Phe Leu Cys
65                  70                  75                  80 gta ttt gcc atc aat aat agc aag tca ttt gcg gat att aac ctc tac     288
Val Phe Ala Ile Asn Asn Ser Lys Ser Phe Ala Asp Ile Asn Leu Tyr
                85                  90                  95 agg gag cag att aag cga gta aaa gac tcg gat gat gta cct atg gtg     336
Arg Glu Gln Ile Lys Arg Val Lys Asp Ser Asp Asp Val Pro Met Val
            100                 105                 110 cta gtg gga aac aag tgt gat ttg cca aca agg aca gtt gat aca aaa     384
Leu Val Gly Asn Lys Cys Asp Leu Pro Thr Arg Thr Val Asp Thr Lys
        115                 120                 125 caa gcc cac gaa ctg gcc aag agt tac ggg att cca ttc att gaa acc     432
Gln Ala His Glu Leu Ala Lys Ser Tyr Gly Ile Pro Phe Ile Glu Thr
    130                 135                 140 tca gcc aag acc aga cag ggt gtt gaa gat gct ttt tac aca ctg gta     480
Ser Ala Lys Thr Arg Gln Gly Val Glu Asp Ala Phe Tyr Thr Leu Val
145                 150                 155                 160 aga gaa ata cgc cag tac cga atg aaa aaa ctc aac agc agt gat gat     528
Arg Glu Ile Arg Gln Tyr Arg Met Lys Lys Leu Asn Ser Ser Asp Asp
                165                 170                 175 ggg act cag ggt tgt atg gga ttg cca tgt gtg gtg atg taa             570
Gly Thr Gln Gly Cys Met Gly Leu Pro Cys Val Val Met
            180                 185

<210> SEQ ID NO 11
<211> LENGTH: 189
<212> TYPE: PRT
<213> ORGANISM: Homo sapiens

<400> SEQUENCE: 11

Met Thr Glu Tyr Lys Leu Val Val Val Gly Ala Gly Gly Val Gly Lys
```

```
                1               5                   10                  15
Ser Ala Leu Thr Ile Gln Leu Ile Gln Asn His Phe Val Asp Glu Tyr
                    20                  25                  30

Asp Pro Thr Ile Glu Asp Ser Tyr Arg Lys Gln Val Val Ile Asp Gly
                    35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                    85                  90                  95

Arg Glu Gln Ile Lys Arg Val Lys Asp Ser Asp Val Pro Met Val
                    100                 105                 110

Leu Val Gly Asn Lys Cys Asp Leu Pro Thr Arg Thr Val Asp Thr Lys
                    115                 120                 125

Gln Ala His Glu Leu Ala Lys Ser Tyr Gly Ile Pro Phe Ile Glu Thr
            130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                    165                 170                 175

Gly Thr Gln Gly Cys Met Gly Leu Pro Cys Val Val Met
                    180                 185

<210> SEQ ID NO 12
<211> LENGTH: 582
<212> TYPE: DNA
<213> ORGANISM: Mus musculus
<220> FEATURE:
<221> NAME/KEY: CDS
<222> LOCATION: (1)..(582)

<400> SEQUENCE: 12 atg act gag tac aaa ctg gtg gtg gtt gga gca ggt ggt gtt ggg aaa      48
Met Thr Glu Tyr Lys Leu Val Val Val Gly Ala Gly Gly Val Gly Lys
1               5                   10                  15 agc gcc ctg acg atc cag cta atc cag aac cac ttt gtg gat gaa tat      96
Ser Ala Leu Thr Ile Gln Leu Ile Gln Asn His Phe Val Asp Glu Tyr
                    20                  25                  30 gat ccc acc ata gag gat tct tac cga aag caa gtg gtg att gat ggt     144
Asp Pro Thr Ile Glu Asp Ser Tyr Arg Lys Gln Val Val Ile Asp Gly
                35                      40                  45 gag acc tgc ctg ctg gac ata ctg gac aca gct gga caa gag gag tac     192
Glu Thr Cys Leu Leu Asp Ile Leu Asp Thr Ala Gly Gln Glu Glu Tyr
        50                  55                  60 agt gcc atg aga gac cag tac atg agg aca ggc gaa ggg ttc ctc tgt     240
Ser Ala Met Arg Asp Gln Tyr Met Arg Thr Gly Glu Gly Phe Leu Cys
65                  70                  75                  80 gta ttt gcc atc aat aat agc aaa tca ttt gca gat att aac ctc tac     288
Val Phe Ala Ile Asn Asn Ser Lys Ser Phe Ala Asp Ile Asn Leu Tyr
                    85                  90                  95 agg gag caa att aag cgt gtg aaa gat tct gat gat gtc ccc atg gtg     336
Arg Glu Gln Ile Lys Arg Val Lys Asp Ser Asp Asp Val Pro Met Val
                    100                 105                 110 ctg gta ggc aac aag tgt gac ttg cca aca agg aca gtt gac aca aag     384
Leu Val Gly Asn Lys Cys Asp Leu Pro Thr Arg Thr Val Asp Thr Lys
                115                 120                 125 caa gcc cac gaa ctg gcc aag agt tac gga att cca ttc att gag acc     432
Gln Ala His Glu Leu Ala Lys Ser Tyr Gly Ile Pro Phe Ile Glu Thr
```

```
                 130                135                140
tca gcc aag acc cga cag ggt gtg gag gat gcc ttt tac aca ctg gta    480
Ser Ala Lys Thr Arg Gln Gly Val Glu Asp Ala Phe Tyr Thr Leu Val
145                 150                155                160 agg gag ata cgc cag tac cga ttg aaa aag ctc aac agc agt gac gat    528
Arg Glu Ile Arg Gln Tyr Arg Leu Lys Lys Leu Asn Ser Ser Asp Asp
                165                170                175 ggc act caa ggt tgt atg ggg tcg ccc tgt gtg ctg atg tgt aag aca    576
Gly Thr Gln Gly Cys Met Gly Ser Pro Cys Val Leu Met Cys Lys Thr
            180                185                190 ctt tga                                                             582
Leu

<210> SEQ ID NO 13
<211> LENGTH: 193
<212> TYPE: PRT
<213> ORGANISM: Mus musculus

<400> SEQUENCE: 13

Met Thr Glu Tyr Lys Leu Val Val Val Gly Ala Gly Gly Val Gly Lys
1               5                  10                 15

Ser Ala Leu Thr Ile Gln Leu Ile Gln Asn His Phe Val Asp Glu Tyr
            20                  25                 30

Asp Pro Thr Ile Glu Asp Ser Tyr Arg Lys Gln Val Val Ile Asp Gly
        35                  40                 45

Glu Thr Cys Leu Leu Asp Ile Leu Asp Thr Ala Gly Gln Glu Glu Tyr
    50                  55                 60

Ser Ala Met Arg Asp Gln Tyr Met Arg Thr Gly Glu Gly Phe Leu Cys
65              70                  75                  80

Val Phe Ala Ile Asn Asn Ser Lys Ser Phe Ala Asp Ile Asn Leu Tyr
            85                  90                 95

Arg Glu Gln Ile Lys Arg Val Lys Asp Ser Asp Asp Val Pro Met Val
        100                 105                110

Leu Val Gly Asn Lys Cys Asp Leu Pro Thr Arg Thr Val Asp Thr Lys
    115                 120                 125

Gln Ala His Glu Leu Ala Lys Ser Tyr Gly Ile Pro Phe Ile Glu Thr
130                 135                 140

Ser Ala Lys Thr Arg Gln Gly Val Glu Asp Ala Phe Tyr Thr Leu Val
145                 150                 155                160

Arg Glu Ile Arg Gln Tyr Arg Leu Lys Lys Leu Asn Ser Ser Asp Asp
                165                 170                 175

Gly Thr Gln Gly Cys Met Gly Ser Pro Cys Val Leu Met Cys Lys Thr
            180                 185                 190

Leu

<210> SEQ ID NO 14
<211> LENGTH: 534
<212> TYPE: DNA
<213> ORGANISM: Homo sapiens
<220> FEATURE:
<221> NAME/KEY: CDS
<222> LOCATION: (1)..(534)

<400> SEQUENCE: 14 atg gtc ctc gac aca gca ggt ttg gag gag tac agt gca atg act gag    48
Met Val Leu Asp Thr Ala Gly Leu Glu Glu Tyr Ser Ala Met Thr Glu
1               5                  10                 15 tat aaa ctt gtg gtg gtt gga gct gtt ggc gta ggc aag agc gcc ttg    96
Tyr Lys Leu Val Val Val Gly Ala Val Gly Val Gly Lys Ser Ala Leu
```

```
                  20                  25                  30
acg ata cag cta att cag aat cac ttt gtg gat gag tac gac cct acg        144
Thr Ile Gln Leu Ile Gln Asn His Phe Val Asp Glu Tyr Asp Pro Thr
         35                  40                  45 ata gag gac tcc tac agg aaa caa gta gta att gat gga gaa acc tgt        192
Ile Glu Asp Ser Tyr Arg Lys Gln Val Val Ile Asp Gly Glu Thr Cys
 50                  55                  60 ctc ttg gat att ctc gac aca gca ggt cga gag gag tac agt gca atg        240
Leu Leu Asp Ile Leu Asp Thr Ala Gly Arg Glu Glu Tyr Ser Ala Met
 65                  70                  75                  80 agg gac cag tac atg aga act ggg gag ggc ttt ctt tgt gta ttt gcc        288
Arg Asp Gln Tyr Met Arg Thr Gly Glu Gly Phe Leu Cys Val Phe Ala
                 85                  90                  95 ata aat aat act aaa tca ttt gaa gat att cac cat tat aga gaa caa        336
Ile Asn Asn Thr Lys Ser Phe Glu Asp Ile His His Tyr Arg Glu Gln
            100                 105                 110 att aaa aga gta aag gac tct gaa gat gtg cct atg gtc ctg gta ggg        384
Ile Lys Arg Val Lys Asp Ser Glu Asp Val Pro Met Val Leu Val Gly
        115                 120                 125 aat aag tgt gat ttg cct tct aga aca gta gac acg aaa cag gct cag        432
Asn Lys Cys Asp Leu Pro Ser Arg Thr Val Asp Thr Lys Gln Ala Gln
130                 135                 140 gag tta gca agg agt tac ggg att ccg ttc att gag acc tca gca aag        480
Glu Leu Ala Arg Ser Tyr Gly Ile Pro Phe Ile Glu Thr Ser Ala Lys
145                 150                 155                 160 aca aga cag ggt gtt gac gat gcc ttc tat aca tta gtc cga gaa att        528
Thr Arg Gln Gly Val Asp Asp Ala Phe Tyr Thr Leu Val Arg Glu Ile
                        165                 170                 175 cga aaa                                                                534
Arg Lys <210> SEQ ID NO 15
<211> LENGTH: 178
<212> TYPE: PRT
<213> ORGANISM: Homo sapiens

<400> SEQUENCE: 15

Met Val Leu Asp Thr Ala Gly Leu Glu Glu Tyr Ser Ala Met Thr Glu
  1               5                  10                  15

Tyr Lys Leu Val Val Val Gly Ala Val Gly Val Gly Lys Ser Ala Leu
                 20                  25                  30

Thr Ile Gln Leu Ile Gln Asn His Phe Val Asp Glu Tyr Asp Pro Thr
             35                  40                  45

Ile Glu Asp Ser Tyr Arg Lys Gln Val Val Ile Asp Gly Glu Thr Cys
         50                  55                  60

Leu Leu Asp Ile Leu Asp Thr Ala Gly Arg Glu Glu Tyr Ser Ala Met
 65                  70                  75                  80

Arg Asp Gln Tyr Met Arg Thr Gly Glu Gly Phe Leu Cys Val Phe Ala
                 85                  90                  95

Ile Asn Asn Thr Lys Ser Phe Glu Asp Ile His His Tyr Arg Glu Gln
            100                 105                 110

Ile Lys Arg Val Lys Asp Ser Glu Asp Val Pro Met Val Leu Val Gly
        115                 120                 125

Asn Lys Cys Asp Leu Pro Ser Arg Thr Val Asp Thr Lys Gln Ala Gln
    130                 135                 140

Glu Leu Ala Arg Ser Tyr Gly Ile Pro Phe Ile Glu Thr Ser Ala Lys
145                 150                 155                 160

Thr Arg Gln Gly Val Asp Asp Ala Phe Tyr Thr Leu Val Arg Glu Ile
```

165                 170                 175
Arg Lys

<210> SEQ ID NO 16
<211> LENGTH: 154
<212> TYPE: PRT
<213> ORGANISM: Homo sapiens

<400> SEQUENCE: 16

Arg Pro Arg Pro Val Leu Arg Ser Val Asn Ser Arg Glu Pro Ser Gln
1               5                   10                  15

Val Ile Phe Cys Asn Arg Ser Pro Arg Val Val Leu Pro Val Trp Leu
            20                  25                  30

Asn Phe Asp Gly Glu Pro Gln Pro Tyr Pro Thr Leu Pro Pro Gly Thr
        35                  40                  45

Gly Arg Arg Ile His Ser Tyr Arg Gly His Leu Trp Leu Phe Arg Asp
    50                  55                  60

Ala Gly Thr His Asp Gly Leu Leu Val Asn Gln Thr Glu Leu Phe Val
65                  70                  75                  80

Pro Ser Leu Asn Val Asp Gly Gln Pro Ile Phe Ala Asn Ile Thr Leu
                85                  90                  95

Pro Val Tyr Thr Leu Lys Glu Arg Cys Leu Gln Val Val Arg Ser Leu
            100                 105                 110

Val Lys Pro Glu Asn Tyr Arg Arg Leu Asp Ile Val Arg Ser Leu Tyr
        115                 120                 125

Glu Asp Leu Glu Asp His Pro Asn Val Gln Lys Asp Leu Glu Arg Leu
    130                 135                 140

Thr Gln Glu Arg Ile Ala His Gln Arg Met
145                 150

<210> SEQ ID NO 17
<211> LENGTH: 154
<212> TYPE: PRT
<213> ORGANISM: Mus musculus

<400> SEQUENCE: 17

Arg Pro Arg Pro Val Leu Arg Ser Val Asn Ser Arg Glu Pro Ser Gln
1               5                   10                  15

Val Ile Phe Cys Asn Arg Ser Pro Arg Val Val Leu Pro Leu Trp Leu
            20                  25                  30

Asn Phe Asp Gly Glu Pro Gln Pro Tyr Pro Ile Leu Pro Pro Gly Thr
        35                  40                  45

Gly Arg Arg Ile His Ser Tyr Arg Gly His Leu Trp Leu Phe Arg Asp
    50                  55                  60

Ala Gly Thr His Asp Gly Leu Leu Val Asn Gln Thr Glu Leu Phe Val
65                  70                  75                  80

Pro Ser Leu Asn Val Asp Gly Gln Pro Ile Phe Ala Asn Ile Thr Leu
                85                  90                  95

Pro Val Tyr Thr Leu Lys Glu Arg Cys Leu Gln Val Val Arg Ser Leu
            100                 105                 110

Val Lys Pro Glu Asn Tyr Arg Arg Leu Asp Ile Val Arg Ser Leu Tyr
        115                 120                 125

Glu Asp Leu Glu Asp Tyr Pro Ser Val Arg Lys Asp Ile Gln Arg Leu
    130                 135                 140

Ser Gln Glu His Leu Glu Ser Gln His Leu
145                 150